(12) United States Patent
Saxena et al.

(10) Patent No.: US 8,974,775 B2
(45) Date of Patent: Mar. 10, 2015

(54) SILICONE IONOMER COMPOSITION

(75) Inventors: Anubhav Saxena, Bangalore (IN); Alok Sarkar, Malda (IN); Sandip Tiwari, Bangalore (IN)

(73) Assignee: Momentive Performance Materials Inc., Waterford, NY (US)

( * ) Notice: Subject to any disclaimer, the term of this patent is extended or adjusted under 35 U.S.C. 154(b) by 13 days.

(21) Appl. No.: 13/343,188

(22) Filed: Jan. 4, 2012

(65) Prior Publication Data

US 2013/0172193 A1    Jul. 4, 2013

(51) Int. Cl.
 *C09D 5/16* (2006.01)
 *A61K 8/89* (2006.01)

(52) U.S. Cl.
 USPC ............ 424/78.09; 424/70.12; 424/401; 424/449; 528/25; 528/26; 528/27; 528/30; 528/31; 528/37

(58) Field of Classification Search
 None
 See application file for complete search history.

(56) References Cited

U.S. PATENT DOCUMENTS

| | | | |
|---|---|---|---|
| 2,968,643 A | 1/1961 | Bailey | |
| 4,523,002 A | 6/1985 | Campbell et al. | |
| 4,525,567 A | 6/1985 | Campbell et al. | |
| 4,532,185 A * | 7/1985 | Balchunis et al. | 428/447 |
| 5,789,628 A * | 8/1998 | Auer et al. | 568/727 |
| 7,005,410 B2 * | 2/2006 | Trinh et al. | 510/287 |
| 7,759,434 B2 | 7/2010 | Funk et al. | |
| 7,838,616 B2 * | 11/2010 | Fukushima et al. | 528/31 |
| 7,875,694 B2 | 1/2011 | Kennan et al. | |
| 2005/0148702 A1 | 7/2005 | Eigen et al. | |
| 2007/0196713 A1 | 8/2007 | Mah et al. | |
| 2008/0293878 A1 | 11/2008 | Funk et al. | |
| 2010/0233113 A1 | 9/2010 | Nguyen et al. | |

FOREIGN PATENT DOCUMENTS

| | | |
|---|---|---|
| CN | 101 468 301 A | 7/2009 |
| EP | 0 581 296 A2 | 2/1994 |
| EP | 0 581 296 A3 | 2/1994 |
| JP | 6247827 A | 9/1994 |
| JP | 6247835 A | 9/1994 |
| WO | 00/78844 A1 | 12/2000 |
| WO | WO2006/065467 A2 | 6/2006 |
| WO | 2006/127924 A2 | 11/2006 |
| WO | WO2010/147759 A2 | 12/2010 |

* cited by examiner

*Primary Examiner* — Marc Zimmer
(74) *Attorney, Agent, or Firm* — Dominick G. Vicari; Joseph S. Ostroff

(57) ABSTRACT

There is provided herein a functionalized ionic silicone composition comprising a silicone of the formula (I):

$$M^1_a M^2_b M^3_c D^1_d D^2_e D^3_f T^1_g T^2_h T^3_i Q_j \quad (I)$$

which contains a monovalent radical bearing ion-pairs and having the formula (II):

-A-I$^{x-}$M$_n^{y+}$; where A is a spacing group having at least 2 spacing atoms selected from a divalent hydrocarbon or hydrocarbonoxy group, where I is an ionic group such as sulfonate —SO$_3^-$, carboxylate —COO$^-$, phosphonate —PO$_3^{2-}$ group and phosphate —OPO$_3^{2-}$, where M is hydrogen or a cation independently selected from alkali metals, alkali earth metals, transition metals, metals, quaternary ammonium and phosphonium groups; or, zwitterions having the formula (III):

$$\text{—R'—NR''}_2{}^+\text{—R'''—I} \quad (III)$$

where I is defined as above, and where the subscript a, b, c, d, e, f, g, h, i, j are zero or positive subject to the following limitations: 2≤a+b+c+d+e+f+g+h+i+j≤6000, b+e+h>0 and c+f+i>0.

33 Claims, No Drawings

SILICONE IONOMER COMPOSITION

TECHNICAL FIELD

The present invention relates to ionic silicone compositions. The present invention also relates to applications containing the ionic silicone composition. In particular, the present invention relates to functionalized ionic silicone compositions.

BACKGROUND OF THE INVENTION

Ionic silicones are siloxane polymers with ionic groups. Siloxane polymers containing ionic groups have been prepared but there exist demands in the marketplace for further ionic silicones which provide for even further uses in various applications.

SUMMARY OF THE INVENTION

One objective of the present invention is directed to a functionalized ionic silicone composition comprising a silicone of the formula (I):

$$M^1_a M^2_b M^3_c D^1_d D^2_e D^3_f T^1_g T^2_h T^3_i Q_j \quad (I)$$

wherein:
$M^1 = R^1 R^2 R^3 SiO_{1/2}$
$M^2 = R^4 R^5 R^6 SiO_{1/2}$
$M^3 = R^7 R^8 R^9 SiO_{1/2}$
$D^1 = R^{10} R^{11} SiO_{2/2}$
$D^2 = R^{12} R^{13} SiO_{2/2}$
$D^3 = R^{14} R^{15} SiO_{2/2}$
$T^1 = R^{16} SiO_{3/2}$
$T^2 = R^{17} SiO_{3/2}$
$T^3 = R^{18} SiO_{3/2}$
$Q = SiO_{4/2}$ where $R^1, R^2, R^3, R^5, R^6, R^8, R^9, R^{10}, R^{11}, R^{13}, R^{15}, R^{16}$ are aliphatic, aromatic or fluoro containing monovalent hydrocarbon radicals containing from 1 to about 60 carbon atoms;

where $R^4$, $R^{12}$, $R^{17}$ are monovalent radical bearing ion-pairs and have the formula (II):

$$-A-I^{x-} M_n^{y+}; \quad (II)$$

where A is a spacing group having at least 2 spacing atoms selected from a divalent hydrocarbon or hydrocarbonoxy group, where I is an ionic group such as sulfonate $—SO_3^-$, sulfate $—OSO_3^{2-}$, carboxylate $—COO^-$, phosphonate $—PO_3^{2-}$ group and phosphate $—OPO_3^{2-}$ group, where M is hydrogen or a cation independently selected from alkali metals, alkali earth metals, transition metals, metals, metal complexes, quaternary ammonium and phosphonium groups, organic cations, alkyl cations, cationic hydrocarbons and cationic biopolymers; or, zwitterions having the formula (III):

$$—R'—NR''_2^+—R'''—I \quad (III)$$

where R' is a divalent hydrocarbon radical containing from 1 to about 20 carbon atoms, where R'' is monovalent hydrocarbon radical containing from 1 to about 20 carbon atoms and where R''' is divalent hydrocarbon radical containing from 2 to about 20 carbon atoms; and, where I is an ionic group such as sulfonate $—SO_3^-$, sulfate $—OSO_3^{2-}$, carboxylate $—COO^-$, phosphonate $—PO_3^{2-}$ and phosphate group $—OPO_3^{2-}$, where $R^7$, $R^{18}$ are independently selected from $—OR^{20}$, hydrogen, unsaturated monovalent radicals or monovalent epoxy group-containing radicals, monovalent sulfur atom-containing radicals and monovalent organosilane groups where $R^{14}$, is independently selected from $—OR^{20}$, unsaturated monovalent radicals or monovalent epoxy group-containing radicals, monovalent sulfur atom-containing radicals and monovalent organosilane groups where $R^{20}$ is a monovalent hydrocarbon radical of from 1 to about 60 carbon atoms when the ionic group is a zwitterion represented by the formula (III) above, where $R^{20}$ is hydrogen, monovalent hydrocarbon radical of from 1 to about 60 carbon atoms otherwise where superscripts n and y are independently from 1 to 6, and where x is a product of n and y where the subscript a, b, c, d, e, f, g, h, i, j are zero or positive subject to the following limitations: the sum a+b+c+d+e+f+g+h+i+j is greater than or equal to 2 and less than or equal to about 6000, b+e+h is greater than zero and c+f+i is greater than zero.

The present invention is further described in the detailed description section provided below.

DETAILED DESCRIPTION OF THE INVENTION

The inventors herein have discovered silicone ionomer polyorganosiloxanes containing ions and at least one functional group as part of their backbone. The functional group of the present invention can undergo various selective physicochemical transformations/modifications to produce silicone ionomers in the form of elastomer, copolymer, gels and emulsion making them very useful in many different applications including personal care, health care, household, paints, coatings, automotive, laundry detergent, textile treatment, oil and gas, fuel cell, electronic application, agriculture, membranes, adhesives, sealants, injection moldable and compression moldable rubbers and plastics, and various silicone based rubbers. The preferred functional groups, other than the ionic groups, can be alkoxy, unsaturated monovalent radicals, radicals containing epoxy groups, radicals containing sulfur atom(s), nitrogen atom(s), oxygen atom(s), radicals containing combinations of the above atoms, or radicals containing organosilane groups.

In the specification and claims herein, the following terms and expressions are to be understood as indicated.

As used in the specification and including the appended claims, the singular forms "a," "an," and "the" include the plural, and reference to a particular numerical value includes at least that particular value, unless the context clearly dictates otherwise.

Ranges expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment.

All methods described herein may be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

As used herein, "comprising," "including," "containing," "characterized by," and grammatical equivalents thereof are inclusive or open-ended terms that do not exclude additional, unrecited elements or method steps, but will also be understood to include the more restrictive terms "consisting of" and "consisting essentially of."

Other than in the working examples or where otherwise indicated, all numbers expressing amounts of materials, reaction conditions, time durations, quantified properties of materials, and so forth, stated in the specification and claims are to be understood as being modified in all instances by the term "about."

It will be understood that any numerical range recited herein includes all sub-ranges within that range and any combination of the various endpoints of such ranges or sub-ranges.

It will be further understood that any compound, material or substance which is expressly or implicitly disclosed in the specification and/or recited in a claim as belonging to a group of structurally, compositionally and/or functionally related compounds, materials or substances includes individual representatives of the group and all combinations thereof.

The expression "aliphatic hydrocarbon" means any hydrocarbon group from which one or more hydrogen atoms has been removed and is inclusive of alkyl, alkenyl, alkynyl, cyclic alkyl, cyclic alkenyl, cyclic alkynyl, aryl, aralkyl and arenyl and may contain heteroatoms.

The term "alkyl" means any monovalent, saturated straight, branched or cyclic hydrocarbon group; the term "alkenyl" means any monovalent straight, branched, or cyclic hydrocarbon group containing one or more carbon-carbon double bonds where the site of attachment of the group can be either at a carbon-carbon double bond or elsewhere therein; and, the term "alkynyl" means any monovalent straight, branched, or cyclic hydrocarbon group containing one or more carbon-carbon triple bonds and, optionally, one or more carbon-carbon double bonds, where the site of attachment of the group can be either at a carbon-carbon triple bond, a carbon-carbon double bond or elsewhere therein. Examples of alkyls include methyl, ethyl, propyl and isobutyl. Examples of alkenyls include vinyl, propenyl, allyl, methallyl, ethylidenyl norbornane, ethylidene norbornyl, ethylidenyl norbornene and ethylidene norbornenyl. Examples of alkynyls include acetylenyl, propargyl and methylacetylenyl.

The expressions "cyclic alkyl", "cyclic alkenyl", and "cyclic alkynyl" include bicyclic, tricyclic and higher cyclic structures as well as the aforementioned cyclic structures further substituted with alkyl, alkenyl, and/or alkynyl groups. Representative examples include norbornyl, norbornenyl, ethylnorbornyl, ethylnorbornenyl, cyclohexyl, ethylcyclohexyl, ethylcyclohexenyl, cyclohexylcyclohexyl and cyclododecatrienyl.

The term "aryl" means any monovalent aromatic hydrocarbon group; the term "aralkyl" means any alkyl group (as defined herein) in which one or more hydrogen atoms have been substituted by the same number of like and/or different aryl (as defined herein) groups; and, the term "arenyl" means any aryl group (as defined herein) in which one or more hydrogen atoms have been substituted by the same number of like and/or different alkyl groups (as defined herein). Examples of aryls include phenyl and naphthalenyl. Examples of aralkyls include benzyl and phenethyl. Examples of arenyls include tolyl and xylyl.

It will be understood herein that all measures of viscosity are obtained at 25 degrees Celsius unless noted otherwise.

Reference is made to substances, components, or ingredients in existence at the time just before first contacted, formed in situ, blended, or mixed with one or more other substances, components, or ingredients in accordance with the present disclosure. A substance, component or ingredient identified as a reaction product, resulting mixture, or the like may gain an identity, property, or character through a chemical reaction or transformation during the course of contacting, in situ formation, blending, or mixing operation if conducted in accordance with this disclosure with the application of common sense and the ordinary skill of one in the relevant art (e.g., chemist). The transformation of chemical reactants or starting materials to chemical products or final materials is a continually evolving process, independent of the speed at which it occurs. Accordingly, as such a transformative process is in progress there may be a mix of starting and final materials, as well as intermediate species that may be, depending on their kinetic lifetime, easy or difficult to detect with current analytical techniques known to those of ordinary skill in the art.

In one non-limiting embodiment of the present invention, there is provided a functionalized ionic silicone composition comprising a silicone of the formula (I):

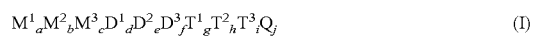

wherein:
$M^1 = R^1R^2R^3SiO_{1/2}$
$M^2 = R^4R^5R^6SiO_{1/2}$
$M^3 = R^7R^8R^9SiO_{1/2}$
$D^1 = R^{10}R^{11}SiO_{2/2}$
$D^2 = R^{12}R^{13}SiO_{2/2}$
$D^3 = R^{14}R^{15}SiO_{2/2}$
$T^1 = R^{16}SiO_{3/2}$
$T^2 = R^{17}SiO_{3/2}$
$T^3 = R^{18}SiO_{3/2}$
$Q = SiO_{4/2}$ where $R^1, R^2, R^3, R^5, R^6, R^8, R^9, R^{10}, R^{11}, R^{13}, R^{15}, R^{16}$ are aliphatic, aromatic or fluoro containing monovalent hydrocarbon radicals containing from 1 to about 60 carbon atoms, specifically from 1 to about 20 carbon atoms and more specifically from 1 to about 8 carbon atoms;

where $R^4$, $R^{12}$, $R^{17}$ are monovalent radical bearing ion-pairs and have the formula (II):

$$-A-I^{x-}M_n^{y+};\qquad (II)$$

where A is a spacing group having at least one spacing atoms selected from a divalent hydrocarbon or hydrocarbonoxy group, where I is an ionic group such as sulfonate —$SO_3^-$, sulfate —$OSO_3^{2-}$, carboxylate —$COO^-$, phosphonate —$PO_3^{2-}$ and phosphate —$OPO_3^{3-}$ group, more specifically sulfonate —$SO_3^-$, where M is hydrogen or a cation independently selected from alkali metals, alkali earth metals, transition metals, metals, metal complexes, quaternary ammonium and phosphonium groups; or, zwitterions having the formula (III):

$$-R'-NR''_2{}^+-R'''-I\qquad (III)$$

where R' is a divalent hydrocarbon radical containing from 1 to about 60 carbon atoms, specifically from 1 to about 20 carbon atoms, and more specifically from 1 to about 8 carbon atoms, where R" is monovalent hydrocarbon radical containing from 1 to about 60 carbon atoms, specifically from 1 to about 20 carbon atoms and more specifically from 1 to about 8 carbon atoms, and where R''' is divalent hydrocarbon radical containing from 2 to about 20 carbon atoms, specifically from 2 to about 8 carbon atoms and more specifically from 2 to about 4 carbon atoms; and, where I is an ionic group such as sulfonate —$SO_3^-$, sulfate —$OSO_3^{2-}$, carboxylate —$COO^-$, phosphonate —$PO_3^{2-}$ group and phosphate —$OPO_3^{2-}$ group.

where $R^7$, $R^{18}$ are independently selected from hydrogen, —$OR^{20}$, unsaturated monovalent radicals or monovalent epoxy group-containing radicals, monovalent sulfur atom-containing radicals and monovalent organosilane groups, where $R^{14}$ are independently selected from $OR^{20}$, unsaturated monovalent radicals or monovalent epoxy group-containing radicals, monovalent sulfur atom-containing radicals and monovalent organosilane groups, where $R^{20}$ is a monovalent hydrocarbon radical of from 1 to about 60 carbon atoms specifically from 1 to about 20 carbon atoms, more specifically from 1 to about 8 carbon atoms, when the ionic group is a zwitterion represented by the formula (III) above, where $R^{20}$ is hydrogen, monovalent hydrocarbon radical of from 2 1 to about 60 specifically from 1 to about 20 carbon atoms, more specifically from 1 to about 8 carbon atoms otherwise where superscripts n and y are independently from 1 to 6 and x is a product of n and y, where the subscript a, b, c, d, e, f, g, h, i, j are zero or positive subject to the following limitations: the sum a+b+c+d+e+f+g+h+i+j is greater than or equal to 2 and less than or equal to 6000, specifically a+b+c+d+e+f+g+h+i+j is greater than or equal to 2 and less than or equal to 4000, more specifically a+b+c+d+e+f+g+h+i+j is less than or equal to 2000, b+e+h is greater than 0 and c+f+i is greater than 0.

In one embodiment herein the monovalent hydrocarbon radical of $R^1$, $R^2$, $R^3$, $R^5$, $R^6$, $R^8$, $R^9$, $R^{10}$, $R^{11}$, $R^{13}$, $R^{15}$, $R^{16}$ is independently selected from the group consisting of methyl, ethyl, n-propyl, iso-propyl, n-butyl, isobutyl, tert-butyl, n-pentyl, iso-pentyl, neopentyl, tert-pentyl, hexyl, such as the n-hexyl group, heptyl, such as the n-heptyl group, octyl, such as the n-octyl and isooctyl groups, 2,2,4-trimethylpentyl, nonyl, such as the n-nonyl group, decyl, such as the n-decyl group, cycloalkyl radicals, such as cyclopentyl, cyclohexyl, cycloheptyl and methylcyclohexyl, and aryl groups such as phenyl, naphthyl; o-, m- and p-tolyl, xylyl, ethylphenyl, and benzyl.

In one other embodiment herein the divalent hydrocarbon group of A in formula (II) is an arylene group selected from the group consisting of divalent hydrocarbon group is an arylene group selected from the group consisting of —(CHR')$_k$C$_6$H$_4$(CH$_2$)$_l$—, —CH$_2$CH(R')(CH$_2$)$_k$C$_6$H$_4$—, and —CH$_2$CH(R')(CH$_2$)$_l$C$_6$H$_3$R"— where R' is a hydrogen or defined by $R^1$, R" is a monovalent radical specifically from about 1 to about 20 carbon atoms, more specifically from about 1 to about 8 carbon atoms, sulfur atom(s), nitrogen atom(s), oxygen atom(s) or a radical containing combinations of the above atoms, where l has a value of 0 to 20, and k has a value of 0 to 20, specifically from 0 to about 10.

In another embodiment, the divalent hydrocarbon group of A in formula (II) is an alkylene group of the formula —(CHR$^{19}$)$_m$— where m has a value of 1 to 20, specifically, from 1 to about 10 and $R^{19}$ is hydrogen or $R^1$.

In another embodiment the divalent hydrocarbonoxy group of A in formula (II) is selected from —(CHR$^{19}$)$_m$—(O—CH(R$^{19}$)CH$_2$—O)$_{m'}$—(CH$_2$)$_l$— where l has a value of from 1 to 20, specifically from 1 to about 10, m has a value of 0 to 50 and m' has the value from 0 to 50.

In one other embodiment, in formula (II) M can be a cation independently selected from Li, Na, K, Cs, Mg, Ca, Ba, Zn, Cu, Fe, Ni, Ga, Al, Mn, Cr, Ag, Au, Pt, Pd, Pb, Sb, Ru, Sn and Rh. One skilled in the art can understand that the cations are not limited to the above said, and also can exist in multivalent forms e.g Mn+2 and Mn+3.

In another embodiment in formula (III) $R^7$, $R^{14}$ and $R^{18}$ are a monovalent hydrocarbon radical selected from the group of the formulae (I) to (IX)

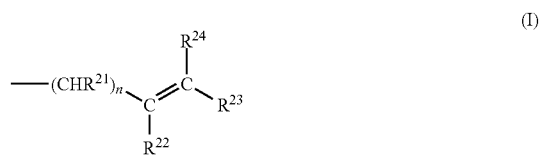

(I)

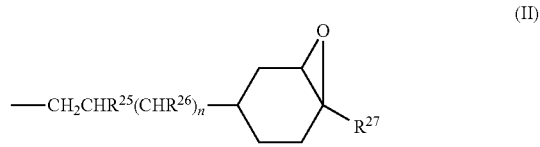

(II)

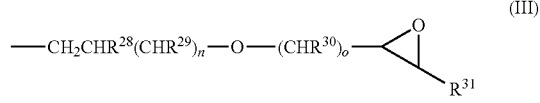

(III)

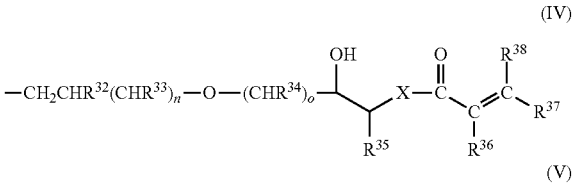

(IV)

(V)

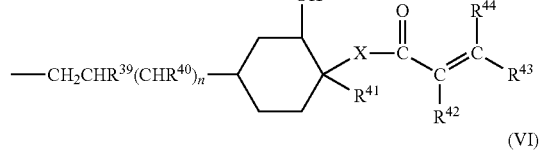

(VI)

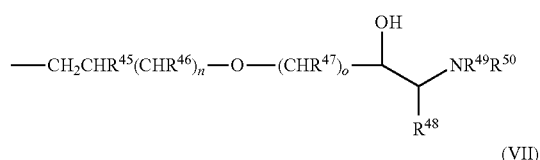

(VII)

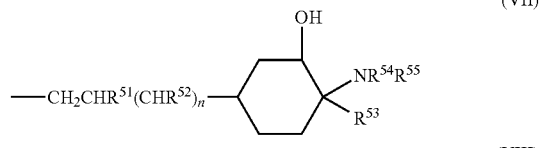

(VIII)

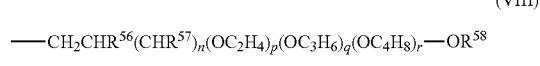

(IX)

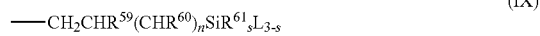

(X)

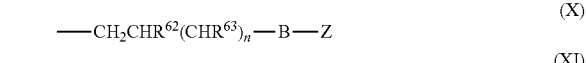

(XI)

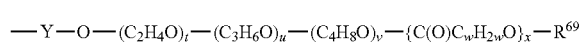

where $R^{21}$, $R^{26}$, $R^{29}$, $R^{30}$, $R^{33}$, $R^{34}$, $R^{40}$, $R^{46}$, $R^{47}$, $R^{52}$, $R^{63}$ are independently selected from —H, —OH, —$R^{66}$ and aliphatic/aromatic monovalent hydrocarbon having from 1 to about 60 carbon atoms;

where $R^{22}$, $R^{23}$, $R^{24}$, $R^{25}$, $R^{27}$, $R^{28}$, $R^{31}$, $R^{32}$, $R^{35}$, $R^{36}$, $R^{37}$, $R^{38}$, $R^{39}$, $R^{41}$, $R^{42}$, $R^{43}$, $R^{44}$, $R^{45}$, $R^{48}$, $R^{51}$, $R^{53}$, $R^{56}$, $R^{57}$, $R^{59}$, $R^{60}$, $R^{61}$, $R^{62}$, are independently selected from hydrogen, aliphatic/aromatic monovalent hydrocarbon having from 1 to about 60 carbon atoms, specifically from 1 to about 20 carbon atoms, more specifically from 1 to about 8 carbon atoms;

where $R^{58}$ is aliphatic/aromatic monovalent hydrocarbon having from 2 to about 60 carbon atoms, specifically from 2 to about 20 carbon atoms, more specifically from 2 to about 8 carbon atoms;

where $R^{49}, R^{50}, R^{54}, R^{55}$ are independently selected from —H, —$C_tH_{2t}$OH and aliphatic/aromatic monovalent hydrocarbon having from 1 to 60 carbon atoms, specifically from 1 to about 20 carbon atoms, more specifically from 1 to about 8 carbon atoms, wherein t is a positive integer, specifically from about 1 to about 20, where L is a monovalent radical independently selected from halogen, $OR^{64}$, —CO(O)$R^{65}$, —N=$CR^{66}_2$, —NCO, —NC(O)$R^{67}$, —C≡N, —N=N and —$NR^{68}_2$ where $R^{64}$, $R^{65}, R^{66}, R^{67}, R^{68}$ are independently selected from a group consisting of hydrogen and alkyl, alkenyl, cycloalkyl and aryl containing from 1 to about 60 carbon atoms, specifically from 1 to about 20 carbon atoms, more specifically from 1 to about 8 carbon atoms;

where Z is a monovalent radical independently selected from halogen, $OR^{64A}$, —CO(O)$R^{65}$, —N=$CR^{66}_2$, —NCO, —NC(O)$R^{67}$, —C≡N, —N=N and —$NR^{68A}_2$ where $R^{65}$, $R^{66}, R^{67}$ are independently selected from a group consisting of hydrogen and alkyl, alkenyl, cycloalkyl and aryl containing from 1 to about 60 carbon atoms, specifically from 1 to about 20 carbon atoms, more specifically from 1 to about 8 carbon atoms and $R^{64A}$ is hydrogen or selected from a group consisting of alkyl, alkenyl, cycloalkyl and aryl containing from 1 to about 60 carbon atoms, specifically from 1 to about 20 carbon atoms, more specifically from 1 to about 8 carbon atoms, and where $R^{68A}$ is selected from a group consisting of alkenyl, cycloalkyl and aryl containing from 1 to about 60 carbon atoms, specifically from 1 to about 20 carbon atoms, more specifically from 1 to about 8 carbon atoms;

where X is divalent radical selected from —$CHR^{65}$—, —O—, —$NR^{65}$— and —S— linkages, where Y and B are divalent radical selected from a linear, branched, cyclic hydrocarbon radical or aralkyl radical containing from 1 to about 60 carbon atoms, specifically from 1 to about 20 carbon atoms, more specifically from 1 to about 8 carbon atoms, and may contain heteroatom;

where $R^{69}$ is hydrogen or a monovalent alkyl radical with 2 to about 20 carbon atoms or a heteroatom, where the subscript n is zero or positive integer and has a value in the range of 0 to about 60, where subscript o is positive integer and has a value in the range of 1 to about 60, where subscripts p, q and r are zero or positive and independently selected from a value in the range of 0 to about 100, subject to the limitation of p+q+r≥1 and s is zero or positive integer and has a value of 0 to about 2, where t, u, v and x can be zero or positive integers subject to the limitation t+u+v+x is greater than or equal to 1 and w is a positive integer.

In one other specific embodiment herein the silicone of formula (I) is selected from the group consisting of sulfonate functional polyorganosiloxane bearing terminal epoxy ether groups, sulfonate functional polyorganosiloxane bearing pendant epoxy ether groups, sulfonate functional polyorganosilxoane bearing pendant alkoxysilane groups, sulfonate functional polyorganosiloxane bearing terminal alkoxysilane groups, sulfonate functional polyorganosiloxane bearing terminal vinyl groups, sulfonate functional polyorganosiloxane bearing terminal polyether groups sulfonate functional polyorganosiloxane bearing terminal silicon-hydride groups, and sulfonate functional polyorganosilxoane bearing terminal acrylate groups.

In yet another specific embodiment herein the silicone of formula (I) is a sulfonate functional polyorganosiloxane bearing any combination of two or more functional groups selected from the group consisting of terminal epoxy ether groups, pendant epoxy ether groups, pendant alkoxysilane groups, terminal alkoxysilane groups, terminal vinyl groups, terminal polyether groups, pendant polyether groups, terminal silicon-hydride groups, pendant silicon-hydride groups, terminal acrylate groups and pendant acrylate groups.

In one other embodiment herein the silicone composition is in a form selected from the group consisting of an elastomer, a copolymer, a gel and an emulsion.

In a more specific embodiment herein there is provided an application containing the functionalized ionic silicone composition described herein, specifically wherein the application is selected from the group consisting of personal care, health care, household, paints, automotive, coatings, laundry detergent, textile treatment, oil and gas, fuel cell, electronic application, agriculture, membranes, adhesives, sealants, injection moldable and compression moldable rubbers and plastics, and various silicone based rubbers.

The level of incorporation of the ionic groups into the functionalized ionic silicones of formula (I) can vary greatly depending upon the specific application in which it is employed, but generally can range from slightly above 0 mol % to about 100 mol %, more specifically from about 0.01 mol % to about 20 mol %, and most specifically from about 0.01 mol % to about 5 mol % of the total weight of the functionalized ionic silicone composition.

The functionalized silicone composition can contain other additives and optional components which are known by those skilled in the art depending on the specific application in which the functionalized silicone composition is employed.

The functionalized silicone composition herein can be formed by combining the silicone of formula (I) with any other components which are known by those skilled in the art, depending on the specific application in which the functionalized silicone composition is employed. Such a combination can take place piece-meal over time or simultaneously.

Furthermore, the functionalized silicone compositions described herein can be prepared (e.g., combined) using either batch, semi-batch or continuous modes of manufacture. Preferably, the ingredients, i.e., the silicone of formula (I) and any other optional components are combined in a continuous compounding extruder or blender or mixer, to produce the functionalized silicone composition. The continuous compounding extruder can be any continuous compounding extruder such as the twin screw Werner-Pfleiderer/ Coperion extruder, or a Buss, or P.B. Kokneader extruder, Banbury mixer, Planetary mixer (e.g. Ross) or any such similar equipment familiar to those skilled in the art.

In the broadest conception of the present invention, all the ingredients may be mixed in the continuous compounding extruder. In such a process, which is continuous, the extruder is operated at a range of from about ambient to about 150 degrees C., but more preferably in the range of from about 60 degrees C. to about 80 degrees C., and even more preferably, the extruder is operated at a partial vacuum so as to remove any volatiles during the mixing process.

The functionalized ionic silicones of the present invention are suitable for many applications in which the known advantageous properties of the silicones and the properties that could be derived from the ionic groups are important, preferably in the fields of healthcare, personal care, agriculture, automobile, electronics/electrical, aerospace, fuel cells, production of domestic appliances, machine and instrument construction, coatings, membranes and adhesives.

Silicones have extensively been used in healthcare applications because of their unique film forming ability, which can provide high oxygen permeability, superior smoothness and greater comfort to the wearer. However, due the lack of the hydrophilicity and water-absorbing property of the silicones, their applications in wound care are very limited (e.g. as backing layer for low exuding wound and scar management). In the wound care industry, there is a growing interest in the development of wound dressings that possess functionality beyond providing physical protection and an optimal moisture environment for the wound. To this end, a dressing material based on a sulfonated tri-block polymer has been reported. This sulfonated polymer possesses an ion-exchange capability that is amenable to binding and controlled release of a variety of therapeutic agents and offers several advantages over existing commercial hydrogels used as wound dressings. These include: (1) excellent film forming properties, (2) hydrophilicity that is proportional to sulfonation level, (3) easy preparation of fabric supported dressings (e.g., polyester, cotton, nylon), (4) excellent mechanical integrity of the materials when hydrated, and (5) stability to a variety of sterilization methodologies. However, synthetic polymers comprised of organic moieties often lack the degree of flexibility or plasticity that is desired for application to a skin surface that it is in constant movement. Materials derived from the functionalized ionic silicones deliver the unique benefits of silicones such as high oxygen permeability and comfort along with high moisture transmission, controlled release of active agents, e.g., silver, antibiotics, growth factors, peptides, proteins and polysaccharides like heparin for the wound care applications.

In addition, the functionalized ionic silicones can also be used for drug delivery applications. Silicones have a long tradition of being used for drug delivery through a wide variety of routes of administration such as transdermal (silicone gels and adhesive films for delivery of anti-inflammatories, analgesics, steroids, hormones and as smoking-cessation devices), mucosal (elastomer rings and plugs for vaginal delivery of contraceptives, anti-viral agents, anti-fungal agents). However, only relatively hydrophobic drugs can be delivered through the silicone matrix. Hydrophilic active agents have been found to slowly crystallize, which reduces their activity and alters the delivery profile of the device. The functional ionic silicones of the present invention, on account of their hydrophilicity can prevent this unwanted crystallization of the drug. Additionally, many drugs can be loaded as bound to the ionic moieties within the silicones, which may further reduce their potential to crystallize and de-activate, thereby increasing shelf-life. Examples of pharmaceutically active ingredients that can be included within the composition include but are not limited to bioactives, anti-acne agents, anti-ageing agents, anti-caries agents, anti-fungal agents, anti-microbial agents, anti-oxidants, anti-cancer, anti-viral, anti-inflammatory, anti-coagulants, hemostatic agents, exfoliants, hormones, hormone analogs, enzymes, proteins and peptides, medicinal compounds, biocides, external analgesics, oral care agents, oral care drugs, oxidizing agents, reducing agents, skin protectants, essential oils, insect repellents, UV light absorbing agents, solar filters, pigments, hydrating agents, vitamins and their combinations thereof.

The composition comprising the above ingredients can be utilized for numerous healthcare applications comprising of drug delivery systems, transdermal patches, wound healing patches, wound dressing patches, transdermal iontophoresis, scaffold for tissue engineering, anti-microbial devices, wound management devices, ophthalmic devices, bioinserts, prostheses and body implants.

It has been established that in control release fertilizer applications, the coatings of ionically and covalently cross-linked polymers act as barrier to water-soluble constituents of the fertilizers, shielding them from premature release in aqueous environments for a long period of time. The benefits obtained by the use of these coatings can include labor savings, increased crop yield, increased nitrogen utilization efficiently and time savings. In this regard, a coating material based on the ionically and covalently cross-linked sulfonated polystyrene and inter-polymer complexes have been reported which can provide sustained release of water soluble constituents of fertilizers through a period ranging from several days to many months. However, the organic sulfonated polymers such as sulfonated polystyrene are highly brittle in nature and the film comprising such polymers can often develop cracks that may result in undesired leaching of the fertilizer constituents. The ionic polysiloxanes of the invention are excellent alternatives as these materials can be made to form highly flexible elastomeric films that are devoid of any defects or cracks. Examples of fertilizers and agricultural materials that can be incorporated within ionic silicone films include but are not limited to: urea, urea ammonium nitrogen, zinc sulfate, ferrous sulfate, ammonium thiosulfate, potassium sulfate, monoammonium phosphate, urea phosphate, calcium nitrate, phosphoric acid, magnesium hydroxide, manganese carbonate, calcium polysulfide, manganese sulfate, calcium chloride, diammonium phosphate, disodium phosphate, monoammonium phosphate, monopotassium phosphate, sodium hexametaphosphate, sodium tripolyphosphate, tetrapotassium pyrophosphate, trisodium phosphate, tetrasodium pyrophosphate, oxides/sulfates of Zn, Mn, Fe, Cu, Mg, boron, boric acid, potassium and sodium salts of boric acid, and sodium molybdate.

Seed coatings, which usually contain a pesticide, fungicide or other active ingredients and film-forming polymer to hold the active ingredients on the seed, are commonly applied to the surface of the seeds to protect them from various microbial and insecticidal activities. The desirable properties of the polymers used in the seed coatings are that they: (a) adhere effectively to the seed surface while providing the uniform coatings, (b) result in a flexible and non-tacky coating with high degree of tear and abrasion resistance, (c) render the coating permeable to moisture, oxygen, visible light, carbon dioxide, and (d) allow the films to retain and release various active ingredients over a prolonged period. Various prior cross-linked organic polymers used as a film former in the prior art for seed coating applications mainly include the cross-linked copolymer of acrylics, modified polyacrylamide and vinyl acrylic resins or the copolymers of polyvinyl acetate, methyl cellulose, etc. However, most of these coatings suffer from the following drawbacks: (a) they are not permeable to gases, (b) they have poor ability to control rate of release of ingredients, and (c) at low temperature (especially in winter season) the coating has a tendency to form discontinuous films which exhibit cracking and flaking. Seed coatings comprising functionalized ionic silicones address many of the problems associated with traditional organic coatings. However, due to the strongly hydrophobic nature of the silicone polymers, the active ingredients, which are mostly hydrophilic in nature, are not compatible with the films and hence can easily get separated out from the films. However, due to the presence of ionic groups the functionalized ionic silicone composition provided herein can deliver the unique film forming benefits of silicones along with the sustained release of actives. The ionic silicone is a novel class of material, which exhibits the unique benefits of silicones with a controllable extent of hydrophilicity and can be used in seed coating applications. Thus, examples of some agents that can be incorporated in seed coatings include pesticides. The term pesticide means any compound used to destroy pests, e.g., rodenticides, insecticides, miticides, fungicides, and herbicides. Illustrative examples of pesticides that can be employed include, but are not limited to, growth regulators, photosynthesis inhibitors, pigment inhibitors, mitotic disrupters, lipid biosynthesis inhibitors, cell wall inhibitors, and cell membrane disrupters. The amount of pesticide employed in compositions of the invention varies with the type of pesticide employed. More specific examples of pesticide compounds that can be used with the compositions of the invention are, but not limited to, herbicides and growth regulators, such as: phenoxy acetic acids, phenoxy propionic acids, phenoxy butyric acids, benzoic acids, triazines and s-triazines, substituted ureas, uracils, bentazon, desmedipham, methazole, phenmedipham, pyridate, amitrole, clomazone, fluridone, norflurazone, dinitroanilines, isopropalin, oryzalin, pendimethalin, prodiamine, trifluralin, glyphosate, sulfonylureas, imidazolinones, clethodim, diclofop-methyl, fenoxaprop-ethyl, fluazifop-p-butyl, haloxyfop-methyl, quizalofop, sethoxydim, dichlobenil, isoxaben, and bipyridylium compounds. Fungicide compositions that can be used with the present invention include, but are not limited to, aldimorph, tridemorph, dodemorph, dimethomorph; flusilazol, azaconazole, cyproconazole, epoxiconazole, furconazole, propiconazole, tebuconazole and the like, imazalil, thiophanate, benomyl carbendazim, chlorothialonil, dicloran, trifloxystrobin, fluoxystrobin, dimoxystrobin, azoxystrobin, furcaranil, prochloraz, flusulfamide, famoxadone, captan, maneb, mancozeb, dodicin, dodine, and metalaxyl. Insecticide, larvacide, miticide and ovacide compounds that can be used with the composition of the present invention include, but are not limited to, *Bacillus thuringiensis*, spinosad, abamectin, doramectin, lepimectin, pyrethrins, carbaryl, primicarb, aldicarb, methomyl, amitraz, boric acid, chlordimeform, novaluron, bistrifluoron, triflumuron, diflubenzuron, imidacloprid, diazinon, acephate, endosulfan, kelevan, dimethoate, azinphos-ethyl, azinphos-methyl, izoxathion, chlorpyrifos, clofentezine, lambda-cyhalothrin, permethrin, bifenthrin, cypermethrin and the like.

The polymer functionalized with anionic groups such as sulfonate, sulfate, carboxylate or phosphate groups can ionically bind basic nitrogen-containing biocides and these polymer-biocide bonds are almost irreversible and very stable in non-polar solvents. In water, however the interaction is weaker and exhibits a larger degree of reversibility. Therefore, when these polymer films are exposed to water, the biocide molecules in the surface layer dissociate and desorbs from the polymer. This unique combination of properties, make these materials highly attractive for antifouling paint applications where slow and sustained release of the biocide ingredients is an essential requirement. Recently, organic polymers functionalized with different anionic groups have been used in antifouling paint applications which show improved performance with respect to the distribution and fixation of the biocide in the paint matrix. Silicone-based paints on the other hand offer some benefits including resistance to heat and weathering, water repellency, superior smoothness etc., which are not available from the organic polymers-based paints. However, use of the ionically modified silicone composition of the invention achieves superior distribution and fixation of the biocides in the paint while retaining the benefits of silicone. Examples of antifouling agents that can be incorporated within the composition include, but are not limited to: metal ions such as copper, silver, zinc, tin, organotin compounds, cationic agents such as chlorhexidine, poly(hexamethylene biguanide), Tralopyril, zinc pyrithione, copper thiocyanate, copper(I)oxide, Dichlofivanid, copper pyrithione, 4,5-dichloro-2-octyl-2H-isothiazole-3-on, benzalkonium chloride, or Zineb.

The functionalized ionic silicone composition of the present invention can also be utilized in personal care for providing transfer resistance, moisturization and control delivery of various personal care ingredients.

The ionic groups of the present invention are hydrophilic in nature, and the films formed from these compositions have high flexibility on account of them being polyorganosiloxanes. Because of this unique combination of properties, these compositions can provide the flexibility to develop personal care formulations along that has the advantages of high transfer resistance, gloss, comfort, and control delivery of actives.

The personal care formulations comprising of the present composition can contain surfactants, emulsifiers, solvents, emollients, moisturizers, humectants, pigments, colorants, fragrances, biocides, preservatives, chelating agents, antioxidants, anti-microbial agents, anti-fungal agents, antiperspirant agents, exfoliants, hormones, hormone analogs, enzymes, proteins and peptides, medicinal compounds, vitamins, alpha-hydroxy acids, beta-hydroxy acids, retinols, niacinamide, skin lightening agents, salts, electrolytes, alcohols, polyols, absorbing agents for ultraviolet radiation, botanical extracts, organic oils, waxes, thickening agents, particulate fillers, silicones, clays, plasticizers, occlusives, sensory enhancers, esters, resins, film formers, film forming emulsifiers, high refractive index materials and their combinations thereof.

Further, the personal care compositions comprising of the present invention can find application as antiperspirant/deodorants, including sprays, sticks and roll-on products, shaving products, skin lotions, moisturizers, toners, bath products, cleansing products, shampoos, conditioners, combined shampoo/conditioners, mousses, styling gels, hair sprays, hair dyes, hair color products, hair bleaches, waving products, hair straighteners, nail polish, nail polish remover, nail creams and lotions, cuticle softeners, sunscreen, insect repellent, anti-aging products, lipsticks, foundations, face powders, eye liners, eye shadows, blushes, makeup, mascaras, moisturizing preparations, foundations, body and hand preparations, skin care preparations, face and neck preparations, tonics, dressings, hair grooming aids, aerosol fixatives, fragrance preparations, aftershaves, make-up preparations, soft focus applications, night and day skin care preparations, non-coloring hair preparations, tanning preparations, synthetic and non-synthetic soap bars, hand liquids, nose strips, non-woven applications for personal care, baby lotions, baby baths and shampoos, baby conditioners, shaving preparations, cucumber slices, skin pads, make-up removers, facial cleansing products, cold creams, sunscreen products, mousses, spritzes, paste masks and muds, face masks, colognes and toilet waters, hair cuticle coats, shower gels, face and body washes, personal care rinse-off products, gels, foam baths, scrubbing cleansers, astringents, nail conditioners, eye shadow sticks, powders for face or eye, lip balms, lip glosses, hair care pump sprays and other non-aerosol sprays, hair-frizz-control gels, hair leave-in conditioners, hair pomades, hair de-tangling products, hair fixatives, hair bleach products, skin lotions, pre-shaves and pre-electric shaves, anhydrous creams and lotions, oil/water, water/oil, multiple and macro and micro emulsions, water-resistant creams and lotions, anti-acne preparations, mouth-washes, massage oils, toothpastes, clear gels and sticks, ointment bases, topical wound-healing products, aerosol talcs, barrier sprays, vitamin and anti-aging preparations, herbal-extract preparations, bath salts, bath and body milks, hair styling aids, hair-, eye-, nail- and skin-soft solid applications, controlled-release personal care products, hair conditioning mists, skin care moisturizing mists, skin wipes, pore skin wipes, pore cleaners, blemish reducers, skin exfoliators, skin desquamation enhancers, skin towelettes and cloths, depilatory preparations, personal care lubricants, nail coloring preparations, sunscreens, cosmetics, hair care products, skin care products, toothpastes, drug delivery systems for topical application of medicinal compositions that are to be applied to the skin and combinations comprises at least one of the foregoing applications.

EXAMPLES

The examples below are provided for the purpose of illustrating the present invention. In all the examples, the structures of the products and intermediates were confirmed through proton and $^{29}$Si NMR.

Example 1

Sulfonic Acid Functionalized Tetramethyldisiloxane

A three necked 500 mL flask was charged with 18.16 g (154.0 mmol) alpha-methylstyrene and $27.2 \times 10^{-5}$ g platinum catalyst. The temperature of the resulting mixture was brought to 115 degrees Celsius, then 9.40 g (70.0 mmol) 1,1,3,3 tetramethyldisiloxane was added drop wise and continued to stir until completion of the hydrosilylation reaction. The complete hydrosilylation was indicated by the disappearance of silicone hydride peak in the $^1$H NMR. The resulting mixture was vacuum stripped to remove unreacted alpha-methylstyrene by placing on an oil bath at 150 degrees Celsius for 2 h which gave 23.2 g aralkylene substituted disiloxane. (Yield: 90%).

To this aralkylene substituted disiloxane (23.2 g, 62.4 mmol), 29.6 g (252.8 mmol) of chlorosulfonic acid was added drop wise through a period of 30 minutes while the mixture being stirred at room temperature. The resulting mixture was continued to stir for additional 30 minutes. The completion of the reaction was determined by $^1$H NMR where total sulfonation of the aromatic ring was indicated by the disappearance of para-substituted aromatic proton peak. The vacuum stripping of the reaction mixture at low pressure afforded 33.0 g of the sulfonated disiloxane as brown viscous oil.

$^1$H NMR: (ppm) 0.02 (s, 12H), 1.07 (d, 4H), 1.31 (d, 6H), 3.02 (q, 2H), 7.36 (d, 4H), 7.75 (d, 4H). $^{29}$Si NMR: (ppm) 6.9.

Example 2

Sulfonic Acid Functionalized Tetramethyltetracyclosiloxane

A three necked 500 mL flask was charged with 70.08 g (60.0 mmol) alpha-methylstyrene and $10.0 \times 10^{-4}$ g platinum catalyst. The temperature of the resulting mixture was brought to 115 degrees Celsius, then 30.0 g (120.5 mmol) 1,3,5,7-tetramethylcyclotetrasiloxane was added drop wise and continued to stir. The progress of the reaction mixture was monitored by $^1$H NMR. After 12 h of the reaction, complete conversion of silicone hydride was indicated by the NMR. Then, the reaction mixture was vacuum stripped at 150 degrees Celsius for 2 h to remove unreacted alpha-methylstyrene which gave 80.5 g aralkylene substituted cyclotetrasiloxane. (Yield: (95%).

To 14.24 g (20.0 mmol) of the above aralkylene substituted cyclotetrasiloxane, 18.64 g (160.0 mmol) chlorosulfonic acid dissolved in 4.0 mL dichloromethane was added drop wise through a period of 30 minutes while the mixture being stirred at room temperature. The resulting mixture was continued to stir for an additional 30 minutes. The completion of the reaction was indicated by $^1$H NMR where complete sulfonation of the aromatic ring was indicated by the disappearance of para-substituted aromatic proton peak. The vacuum stripping of the reaction mixture at low pressure afforded 20.6 g of the sulfonic acid functional cyclotetrasiloxane as brown viscous gum.

$^1$H NMR: (ppm) −0.08 (s, 12H), 1.05 (m, 8H), 1.32 (m, 12H), 3.03 (m, 4H), 7.36 (d, 8H), 7.76 (d, 8H). $^{29}$Si NMR: (ppm) −23.0, −20.5.

Example 3

Sodium Salt of Sulfonic Acid Functional Polyorganosiloxane Bearing Terminal Hydride Groups To the sulfonic acid functional cyclotetrasiloxane 20.6 g (20.0 mmol) obtained in Example 2, 587.26 g (1980.0 mmol) octamethyltetracyclosiloxane and 3.54 g (26.4 mmol) 1,1,3, 3-tetramethyldisiloxane were added and continued to stir at room temperature. After reaching an equilibrium of ~87 wt % of the linear siloxanes, the reaction mixture was neutralized using 26.9 (320.0 mmol) moistened sodium bicarbonate at 70 degrees Celsius. The vacuum stripping of the reaction mixture at low pressure afforded 542.0 g (85%) of the product as viscous gum. The NMR analysis of the product indicated that the polymer is a sodium salt of sulfonic acid functional polydimethylsiloxane bearing terminal group. The polymer had a viscosity of 47.5 Pas at a shear rate of 10 rad/s when measured by a HAAKE Rheometer at 20 degrees Celsius.

Example 4

Sodium Salt of Sulfonic Acid Functional Polyorganosiloxane Bearing Terminal Epoxy Ether Groups To the hydride-terminated sulfonated polydimethylsiloxane 118.4 g (5.0 mmol) obtained in Example 3, 100.0 mL toluene, 1.48 g (13.0 mmol) allylglycidyl ether and $1.20 \times 10^{-3}$ g of platinum catalyst were added and continued to reflux at 100 degrees Celsius for 12 h. At this point, the complete reaction of the silicon-hydride bond with the allylglycidyl ether molecules was indicated by $^1$H NMR. The vacuum stripping of the reaction mixture at low pressure afforded 119.5 g of the product a viscous gum. The NMR analysis of the product indicated that the polymer is a sodium salt of sulfonic acid functional polydimethylsiloxane bearing terminal epoxy ether groups. The polymer had a viscosity of 201.5 Pas at a shear rate of 10 rad/s when measured by a HAAKE Rheometer at 20 degrees Celsius.

Example 5

Sodium Salt of Sulfonic Acid Functional Polyorganosiloxane Bearing Terminal Epoxy Groups To the hydride-terminated sulfonated polydimethylsiloxane 11.8 g (0.5 mmol) obtained in Example 3, 20.0 mL toluene, 0.16 g (1.3 mmol) 1,2-epoxy-4-vinylcyclohexene and $1.20\times10^{-4}$ g of platinum catalyst were added and continued to reflux at 100 degrees Celsius for 12 h. At this point, the complete reaction of the silicon-hydride bond with the vinylcyclohexyl epoxide molecules was indicated by $^1$H NMR. The vacuum stripping of the reaction mixture at low pressure afforded 11.9 g of the product an as viscous gum. The NMR analysis of the product indicated that the polymer is a sodium salt of sulfonic acid functional polydimethylsiloxane bearing terminal epoxy groups. The polymer had a viscosity of 70.0 Pas at a shear rate of 10 rad/s when measured by a HAAKE Rheometer at 20 degrees Celsius.

Example 6

Sodium Salt of Sulfonic Acid Functional Polyorganosiloxane Bearing Pendant Epoxy Ether Groups To the sulfonic acid functional disiloxane 8.38 g (15.8 mmol) obtained in Example 1, 468.63 g (1580.0 mmol) octamethyltetracyclosiloxane and 3.72 g (15.8 mmol) 1,3,5,7-tetramethylcyclotetrasiloxane were added and continued to stir at room temperature. After reaching an equilibrium of ~87 wt % of the linear siloxanes, the reaction mixture was neutralized using 10.6 (126.0 mmol) moistened sodium bicarbonate at 70 degrees Celsius. The vacuum stripping of the reaction mixture at low pressure afforded 541.4 g of the product as viscous gum. The NMR analysis of the product indicated that the polymer is a sodium salt of sulfonic acid functional polydimethylsiloxane bearing pendant hydride groups.

To 29.6 g (1.0 mmol) of the above product, 50.0 mL toluene, 0.59 g (5.2 mmol) allylglycidyl ether and $4.0\times10^{-4}$ g of platinum catalyst were added and continued to reflux at 100 degrees Celsius for 12 h. The vacuum stripping of the reaction mixture at low pressure afforded 29.9 g the product as viscous gum. The NMR analysis of the product has indicated the polymer is a sodium salt of sulfonic acid functional polydimethylsiloxane bearing pendant epoxy ether groups.

Example 7

Sodium Salt of Sulfonic Acid Functional Polyorganosiloxane Bearing Pendant Hydride and Epoxy Ether Groups To the sulfonic acid functional disiloxane 8.38 g (15.8 mmol) obtained in Example 1, 468.63 g (1580.0 mmol) octamethyltetracyclosiloxane and 3.72 g (15.8 mmol) 1,3,5,7-tetramethylcyclotetrasiloxane were added and continued to stir at room temperature. After reaching an equilibrium of ~87 wt % of the linear siloxanes, the reaction mixture was neutralized using 10.6 (126.0 mmol) moistened sodium bicarbonate at 70 degrees Celsius. The vacuum stripping of the reaction mixture at low pressure afforded 541.4 g of the product as viscous gum. The NMR analysis of the product indicated that the polymer is a sodium salt of sulfonic acid functional polydimethylsiloxane bearing pendant hydride groups.

To 29.6 g (1.0 mmol) of the above product, 50.0 mL toluene, 0.22 g (2.0 mmol) allylglycidyl ether and $4.0\times10^{-4}$ g of platinum catalyst were added and continued to reflux at 100 degrees Celsius for 12 h. The vacuum stripping of the reaction mixture at low pressure afforded 29.8 g the product as viscous gum. The NMR analysis of the product has indicated the polymer is a sodium salt of sulfonic acid functional polydimethylsiloxane bearing pendant hydride and epoxy ether groups.

Example 8

Sodium Salt of Sulfonic Acid Functional Polyorganosiloxane Bearing Pendant Alkoxysilane Groups To the sulfonic acid functional disiloxane 8.38 g (15.8 mmol) obtained in Example 1, 468.63 g (1580.0 mmol) octamethyltetracyclosiloxane and 3.72 g (15.8 mmol) 1,3,5,7-tetramethylcyclosiloxane were added and continued to stir at room temperature. After reaching an equilibrium of ~87 wt % of the linear siloxanes, the reaction mixture was neutralized using 10.6 (126.0 mmol) moistened sodium bicarbonate at 70 degrees Celsius. The vacuum stripping of the reaction mixture at low pressure afforded 541.4 g of the product as viscous gum. The NMR analysis of the product indicated that the polymer is a sodium salt of sulfonic acid functional polydimethylsiloxane bearing pendant hydride groups.

To 29.6 g (1.0 mmol) of the above product, 50.0 mL toluene, 0.85 g (5.2 mmol) allyltrimethoxysilane and $4.0\times10^{-4}$ g of platinum catalyst were added and continued to reflux at 100 degrees Celsius for 12 h. The vacuum stripping of the reaction mixture at low pressure afforded 30.3 g of the product as a viscous gum. The NMR analysis of the product has indicated that the polymer is a sodium salt of sulfonic acid functional polydimethylsiloxane bearing pendant trimethoxysilane groups.

Example 9

Sodium Salt of Sulfonic Acid Functional Polyorganosiloxane Bearing Pendant Hydride and Alkoxysilane Groups To the sulfonic acid functional disiloxane 8.38 g (15.8 mmol) obtained in Example 1, 468.63 g (1580.0 mmol) octamethyltetracyclosiloxane and 3.72 g (15.8 mmol) 1,3,5,7-tetramethylcyclotetrasiloxane were added and continued to stir at room temperature. After reaching an equilibrium of ~87 wt % of the linear siloxanes, the reaction mixture was neutralized using 10.6 (126.0 mmol) moistened sodium bicarbonate at 70 degrees Celsius. The vacuum stripping of the reaction mixture at low pressure afforded 541.4 g of the product as viscous gum. The NMR analysis of the product indicated that the polymer is a sodium salt of sulfonic acid functional polydimethylsiloxane bearing pendant hydride groups.

To 29.6 g (1.0 mmol) of the above product, 50.0 mL toluene, 0.32 g (2.0 mmol) allyltrimethoxysilane and $4.0\times10^{-4}$ g of platinum catalyst were added and continued to reflux at 100 degrees Celsius for 12 h. The vacuum stripping of the reaction mixture at low pressure afforded 29.9 g of the product as a viscous gum. The NMR analysis of the product has indicated that the polymer is a sodium salt of sulfonic acid functional polydimethylsiloxane bearing pendant hydride and trimethoxysilane groups.

Example 10

Sodium Salt of Sulfonated Functional Polyorganosiloxane Bearing Terminal Alkoxysilane Groups To the sulfonate functional polydimethylsiloxane bearing terminal hydride groups 59.2 g (2.5 mmol) obtained in Example 3, 50.0 mL toluene, 1.24 g (6.5 mmol) vinyltriethoxysilane 8.0×10$^{-4}$ g of platinum catalyst were added and continued to reflux for 12 h. At this poin, the complete reaction of the silicon-hydride bonds with the vinyltriethoxysilane was indicated by NMR. The vacuum stripping of the reaction mixture at low pressure afforded 65.3 g of the product as a viscous gum. The NMR analysis of the product has indicated that the polymer is a sodium salt of sulfonic acid functional polydimethylsiloxane bearing terminal triethoxysilane groups.

Example 11

Sodium Salt of Sulfonic Acid Functional Polyorganosiloxane Bearing Terminal Polyether Groups To the hydride-terminated sulfonated polydimethylsiloxane 11.8 g (0.5 mmol) obtained in Example 6, 20.0 mL toluene, 0.32 g (1.3 mmol) allylpolyether (PEG AM 250) and 1.20×10$^{-4}$ g of platinum catalyst were added and continued to reflux at 100 degrees Celsius for 12 h. At this point, the complete reaction of the silicon-hydride bond with the allylpolyether molecules was indicated by $^1$H NMR. The vacuum stripping of the reaction mixture at low pressure afforded 12.1 g of the product as waxy solid. The NMR analysis of the product has indicated the polymer is a sodium salt of sulfonic acid functional polydimethylsiloxane bearing the terminal polyether groups. The polymer had a viscosity of 169.3 Pas at a shear rate of 10 rad/s when measured by a HAAKE Rheometer at 20 degrees Celsius.

Example 12

Sodium Salt of Sulfonic Acid Functional Polyorganosiloxane Bearing Terminal Vinyl Groups To the sulfonic acid functional cyclotetrasiloxane 8.26 g (8.0 mmol) obtained in Example 2, 474.7 g (1600.0 mmol) octamethyltetracyclosiloxane and 1.48 g (8.0 mmol) 1,1,3,3-tetramethyl-1,3-divinyldisiloxane were added and continued to stir at room temperature. After reaching equilibrium of ~87 wt % of the linear siloxanes, the reaction mixture was neutralized using 10.8 g (128.0 mmol) moistened sodium bicarbonate at 70 degrees Celsius. The vacuum stripping of the reaction mixture at low pressure afforded 411.0 g of the product as viscous gum. The NMR analysis of the product indicated that the polymer is a sodium salt of sulfonic acid functional polydimethylsiloxane bearing terminal vinyl groups. The polymer had a viscosity of 5.4 Pas at a shear rate of 10 rad/s when measured by a HAAKE Rheometer at 20 degrees Celsius.

Example 13

Sodium Salt of Sulfonic Acid Functional Polyorganosiloxane Bearing Terminal Acrylate Groups To the epoxy-terminated sulfonated polydimethylsiloxane 38.8 g (1.5 mmol) obtained in Example 5, 50.0 mL toluene, 4.2×10$^{-3}$ g of Ti(OPr$^i$)$_4$ catalyst and 3.93×10$^{-5}$ g of 4-hydroxy TEMPO were added. The resulting mixture was heated to 115 degrees Celsius and then 0.43 g of acrylic acid was added drop-wise. The resulting mixture was continued to stir at 115 degrees Celsius for 48 h. The vacuum stripping of the reaction mixture at low pressure afforded 39.0 g of the product as a viscous gum. The NMR analysis of the product has indicated that the polymer is a sodium salt of sulfonic acid functional polydimethylsiloxane bearing terminal acrylate groups. The polymer had a viscosity of 156.9 Pas at a shear rate of 10 rad/s when measured by a HAAKE Rheometer at 20 degrees Celsius.

Example 14

Sodium Salt of Sulfonic Acid Functional Polyorganosiloxane Bearing Pendant Hydride and Polyether Groups To the sulfonic acid functional disiloxane 8.38 g (15.8 mmol) obtained in Example 1, 468.63 g (1580.0 mmol) octamethyltetracyclosiloxane and 3.72 g (15.8 mmol) 1,3,5,7-tetramethylcyclotetrasiloxane were added and continued to stir at room temperature. After reaching an equilibrium of ~87 wt % of the linear siloxanes, the reaction mixture was neutralized using 10.6 (126.0 mmol) moistened sodium bicarbonate at 70 degrees Celsius. The vacuum stripping of the reaction mixture at low pressure afforded 541.4 g of the product as viscous gum. The NMR analysis of the product indicated that the polymer is a sodium salt of sulfonic acid functional polydimethylsiloxane bearing pendant hydride groups.

To 14.8 g (0.5 mmol) of the above product, 20.0 mL toluene, 0.45 g (1.0 mmol) allylpolyether (PEG AM 450) and 1.20×10$^{-4}$ g of platinum catalyst were added and continued to reflux at 100 degrees Celsius for 12 h. The vacuum stripping of the reaction mixture at low pressure afforded 15.1 g of the product as waxy solid. The NMR analysis of the product has indicated the polymer is a sodium salt of sulfonic acid functional polydimethylsiloxane bearing pendant hydride and polyether groups.

Example 15

Sodium Salt of Sulfonic Acid Functional Polyorganosiloxane Bearing Pendant Polyether and Epoxy Groups To the sulfonic acid functional disiloxane 8.38 g (15.8 mmol) obtained in Example 1, 468.63 g (1580.0 mmol) octamethyltetracyclosiloxane and 3.72 g (15.8 mmol) 1,3,5,7-tetramethylcyclotetrasiloxane were added and continued to stir at room temperature. After reaching an equilibrium of ~87 wt % of the linear siloxanes, the reaction mixture was neutralized using 10.6 (126.0 mmol) moistened sodium bicarbonate at 70 degrees Celsius. The vacuum stripping of the reaction mixture at low pressure afforded 541.4 g of the product as viscous gum. The NMR analysis of the product indicated that the polymer is a sodium salt of sulfonic acid functional polydimethylsiloxane bearing pendant hydride groups.

To 14.8 g (0.5 mmol) of the above product, 20.0 mL toluene, 0.45 g (1.0 mmol) allylpolyether (PEG AM 450) and 1.20×10$^{-4}$ g of platinum catalyst were added and continued to reflux at 100 degrees Celsius for 12 h. The vacuum stripping of the reaction mixture at low pressure afforded 15.2 g of the product as waxy solid. The NMR analysis of the product has indicated the polymer is a sodium salt of sulfonic acid functional polydimethylsiloxane bearing pendant hydride and polyether groups.

To 15.2 g (0.5 mmol) of the above product, 20.0 mL toluene, 0.12 g (1.0 mmol) 1,2-epoxy-4-vinylcyclohexene and 1.20×10$^{-4}$ g of platinum catalyst were added and continued to reflux at 100 degrees Celsius for 12 h. The vacuum stripping of the reaction mixture at low pressure afforded 15.3 g of the product as waxy solid. The NMR analysis of the product has indicated the polymer is a sodium salt of sulfonic acid functional polydimethylsiloxane bearing pendant polyether and epoxy groups.

Example 16

Sodium Salt of Sulfonic Acid Functional Polyorganosiloxane Bearing Pendant Hydride and Epoxy Groups To the sulfonic acid functional disiloxane 8.38 g (15.8 mmol) obtained in Example 1, 468.63 g (1580.0 mmol) octamethyltetracyclosiloxane and 3.72 g (15.8 mmol) 1,3,5,7-tetramethylcyclotetrasiloxane were added and continued to stir at room temperature. After reaching an equilibrium of ~87 wt % of the linear siloxanes, the reaction mixture was neutralized using 10.6 (126.0 mmol) moistened sodium bicarbonate at 70 degrees Celsius. The vacuum stripping of the reaction mixture at low pressure afforded 541.4 g of the product as viscous gum. The NMR analysis of the product indicated that the polymer is a sodium salt of sulfonic acid functional polydimethylsiloxane bearing pendant hydride groups.

To 14.8 g (0.5 mmol) of the above product, 20.0 mL toluene, 0.12 g (1.0 mmol) 1,2-epoxy-4-vinylcyclohexene and $1.20 \times 10^{-4}$ g of platinum catalyst were added and continued to reflux at 100 degrees Celsius for 12 h. The vacuum stripping of the reaction mixture at low pressure afforded 14.9 g of the product as waxy solid. The NMR analysis of the product has indicated the polymer is a sodium salt of sulfonic acid functional polydimethylsiloxane bearing pendant hydride and epoxy groups.

Example 17

Sodium Salt of Carboxylic Acid Functional Polyorganosiloxane Bearing Terminal Vinyl Groups A three necked 500 mL round bottom flask was charged with 55.5 g (0.99 M) potassium hydroxide and 200 mL water. Heat the solution to 60 degrees Celsius and add with stirring 49.26 g (0.3M) eugenol and raised the temperature to 100 degrees Celsius. To the above solution was added 45.3 g (0.48M) chloroacetic acid dissolved in 50 mL water over the period of 1 h. The solution was further stirred at 100-105 degrees Celsius for 3 h. At this point the pH of reaction mixture was brought to about 2.0 via addition of dilute HCl (~5M) at a temperature of 80 degrees Celsius. The reaction mixture was further cooled to 10 degrees Celsius when carboxylic acid functional eugenol was obtained as white precipitate. The precipitate was collected, washed and characterized with NMR.

A three necked 500 mL round bottom flask was charged with 8.88 g (0.04M) of the above product, 17 g (0.1M) iodopropane, 100 mL toluene and 14.8 g (0.08M) tributylamine. The solution was heated to 90-95 degrees Celsius and stirred at this temperature for 6 h. The solids formed were separated from the reaction mixture by filtration. The filtrate was collected and thoroughly washed with dilute HCl (1N) then with deionized water. The vacuum stripping of the solution at low pressure afforded ester derivative of the carboxylic acid functional eugenol.

A three necked 500 mL round bottom flask was charged with 11.0 g (0.041M) of the above product and 0.001 g platinum catalyst and heated the solution to 90 degrees Celsius. Added 2.4 g (0.01M) tetramethylcyclotetrasiloxane drop wise in 10 minutes and continued to stir the solution for 16 h to afford carboxylic ester functionalized tetramethylcyclotetrasiloxane.

A three necked 500 ml round bottom flask was charged with 6.5 g (0.005M) of the above product, and 25 mL ethanol and continued to stir. To this solution, 0.8 g (0.02M) sodium hydroxide dissolved in 5 mL water was added and the solution was heated to 80-85 degrees Celsius and continued stir at this temperature for 3 h. The solution was acidified by 6N HCl and then poured into 100 mL water. The product was then extract with 100 mL ethyl acetate, washed with water and vacuum stripped at low pressure to afford carboxylic acid functional tetramethylcyclotetrasiloxane. (Yield: 80%)

A three necked 500 mL round bottom flask was charged with 1.4 g (0.00125M) of the above product, 74 g (0.25M) octamethylcyclotetrasiloxane, 0.46 g (0.0025M) 1,3-divinyl-1,1,3,3-tetramethyldisiloxane and 1.0 g sulphuric acid. The solution was heated to 60° C. and stirred at 60-65 degrees Celsius for 16 h. cool to 50 degrees Celsius and added 200 mL hexane, and 10 g moistened sodium bicarbonate. The resulting slurry was stirred for 6 h at 50-55 degrees Celsius. The solution was filtered, washed with hexane and the filtrate was vacuum stripped at low pressure to afford carboxylate functional polydimethylsiloxane with terminal vinyl group.

Example 18

Sodium Salt of Sulfonic Acid Functional Polyorganosiloxane Bearing Pedant Vinyl Groups To the sulfonic acid functional disiloxane 4.17 g (7.9 mmol) obtained in Example 1, 234.3 g (790.0 mmol) octamethyltetracyclosiloxane and 5.4 g (15.8 mmol) 1,3,5,7-tetramethyl-1,3,5,7 tetravinylcyclotetrasiloxane were added and continued to stir at room temperature. After reaching an equilibrium of ~87% the reaction mixture was neutralized using 5.3 (63.0 mmol) moistened sodium bicarbonate at 70 degrees Celsius. The vacuum stripping of the reaction mixture at low pressure afforded 215.0 g of the product as viscous gum. The NMR analysis of the product indicated that the polymer is a sodium salt of sulfonic acid functional polydimethylsiloxane bearing pendant vinyl groups. The polymer had a viscosity of 19.3 Pas at a shear rate of 10 rad/s when measured by a HAAKE Rheometer at 20 degrees Celsius.

Example 19

Sodium Salt of Carboxylic Acid Functional Polyorganosiloxane Bearing Terminal hydride Groups A three necked 500 mL round bottom flask was charged with 55.5 g (0.99 M) potassium hydroxide and 200 mL water. Heat the solution to 60 degrees Celsius and add with stirring 49.26 g (0.3M) eugenol and raised the temperature to 100 degrees Celsius. To the above solution was added 45.3 g (0.48M) chloroacetic acid dissolved in 50 mL water over the period of 1 h. The solution was further stirred at 100-105 degrees Celsius for 3 h. At this point the pH of reaction mixture was brought to about 2.0 via addition of dilute HCl (~5M) at a temperature of 80 degrees Celsius. The reaction mixture was further cooled to 10 degrees Celsius when carboxylic acid functional eugenol was obtained as white precipitate. The precipitate was collected, washed and characterized with NMR.

$^1$H NMR: (ppm) 3.25 (d, 2H), 3.63 (s, 3H), 4.25 (s, 2H), 5.15 (d, 2H), 5.90 (m, 1H), 6.45-6.70 (m, 3H)

A three necked 500 mL round bottom flask was charged with 8.88 g (0.04M) of the above product, 17 g (0.1M) iodopropane, 100 mL toluene and 14.8 g (0.08M) tributylamine. The solution was heated to 90-95 degrees Celsius and stirred at this temperature for 6 h. The solids formed were separated from the reaction mixture by filtration. The filtrate was collected and thoroughly washed with dilute HCl (1N) then with deionized water. The vacuum stripping of the solution at low pressure afforded ester derivative of the carboxylic acid functional eugenol.

$^1$H NMR: (ppm) 0.92 (m, 3H), 1.70 (m, 2H), 3.38 (m, 2H), 3.90 (s, 3H), 4.19 (s, 2H), 4.70 (s, 2H), 5.10 (d, 2H), 5.95 (m, 1H), 6.65-6.85 (m, 3H)

A three necked 500 mL round bottom flask was charged with 11.0 g (0.041M) of the above product and 0.001 g (50 ppm) platinum catalyst and heated the solution to 90 degrees Celsius. Added 2.4 g (0.01M) tetramethylcyclotetrasiloxane drop wise in 10 minutes and continued to stir the solution for 16 h to afford carboxylic ester functionalized tetramethylcyclotetrasiloxane.

$^1$H NMR: (ppm) 0.05 (m, 12H), 0.59 (m, 8H), 0.95 (m, 12H), 1.65 (m, 16H), 2.59 (m, 8H), 3.85 (m, 12H), 4.15 (m, 8H), 4.65 (s, 8H), 6.60-6.85 (m, 12H)

A three necked 500 ml round bottom flask was charged with 6.5 g (0.005M) of the above product, and 25 mL ethanol and continued to stir. To this solution, 0.8 g (0.02M) sodium hydroxide dissolved in 5 mL water was added and the solution was heated to 80-85 degrees Celsius and continued stir at this temperature for 3 h. The solution was acidified by 6N HCl and then poured into 100 mL water. The product was then extract with 100 mL ethyl acetate, washed with water and vacuum stripped at low pressure to afford carboxylic acid functional tetramethylcyclotetrasiloxane. (Yield: 80%)

$^1$H NMR: (ppm) 0.05 (m, 12H), 0.59 (m, 8H), 1.30 (m, 8H), 2.55 (m, 8H), 3.83 (s, 12H), 4.65 (s, 8H), 6.60-6.85 (m, 12H)

A three necked 500 mL round bottom flask was charged with 1.4 g (0.00125M) of the above product, 74 g (0.25M) octamethylcyclotetrasiloxane, 0.33 g (0.0025M) 1,1,3,3-tetramethyldisiloxane and 1.0 g sulphuric acid. The solution was heated to 60° C. and stirred at 60-65 degrees Celsius for 16 h. cool to 50 degrees Celsius and added 200 mL hexane, and 10 g moistened sodium bicarbonate. The resulting slurry was stirred for 6 h at 50-55 degrees Celsius. The solution was filtered, washed with hexane and the filtrate was vacuum stripped at low pressure to afford carboxylate functional polydimethylsiloxane with terminal hydride group. The polymer had a viscosity of 19.7 Pas at a shear rate of 10 rad/s when measured by a HAAKE Rheometer at 20 degrees Celsius.

Example 20

Sodium Salt of Carboxylic Acid Functional Polyorganosiloxane Bearing Terminal triethoxysilyl Groups A three necked 500 mL round bottom flask was charged with 6 g (0.196 mM) of the product (from example 19), 0.3 g (1.576 mM) vinyltriethoxysilane and 0.001 g chloroplatinic acid. The solution was heated to 80° C. and stirred at 80-90 degrees Celsius for 16 h to afford carboxylate functional polydimethylsiloxane with terminal triethoxysilyl group. The polymer had a viscosity of 27.3 Pas at a shear rate of 10 rad/s when measured by a HAAKE Rheometer at 20 degrees Celsius.

Example 21

Sodium Salt of Carboxylic Acid Functional Polyorganosiloxane Bearing Terminal Polyether Groups A three necked 500 mL round bottom flask was charged with 6 g (0.196 mM) of the product (from example 19), 0.2 g (0.5 mM) allyl terminated polyether (AM450 PEG from Clariant) and 0.001 g chloroplatinic acid. The solution was heated to 80 degrees Celsius and stirred at 80-90 degrees Celsius for 16 h to afford carboxylate functional polydimethylsiloxane with terminal polyether group. The polymer had a viscosity of 21.7 Pa·s at a shear rate of 10 rad/s when measured by a HAAKE Rheometer at 20 degrees Celsius.

Example 22

Phosphate Functional Polyorganosiloxane Bearing Terminal Vinyl Groups

A three necked 500 mL round bottom flask was charged with 24.0 g (0.1M) 1,3,5,7-tetramethylcyclotetrasiloxane, 68.0 g (0.41 M) eugenol and 0.001 g platinum catalyst. The solution was heated to 60 degrees Celsius and stirred for 6 h. The solution was further stirred at 90-100 degrees Celsius for another 6 h to give eugenol functionalized cyclotetrasiloxane derivative.

A three necked 500 mL round bottom flask was charged with 17.9 g (0.02M) of the above product and 4.5 g (0.08 M) potassium hydroxide dissolved in 100 ml water. The solution was heated to 90-95 degrees Celsius and stirred at this temperature for about 2 h till dissolution. The solution was concentrated under vacuum till complete removal of water. 150 ml toluene was added and distilled 50 ml toluene to remove traces of water. The solution was maintained at 80 degrees Celsius while 15.5 g (0.08 M) Diethylchlorophosphate was added drop wise in 15 minutes. The solution was stirred at 80-90 degrees Celsius for 6 h. Solids formed were separated from the reaction mixture by filtration. The filtrate was washed with 2% sodium bicarbonate solution then with water. The vacuum stripping of the solution at low pressure afforded phosphate ester derivative of tetramethylcyclotetrasiloxane.

A three necked 250 mL round bottom flask was charged with 14 g (0.01 M) above product and 50 ml 6M HCl solution. Heat the solution to 90 degrees Celsius and stir for 6 h. The solution was cooled to room temperature and water was removed from the sticky product. The product was washed with water, dissolved in ethyl acetate, dried with sodium sulphate. The vacuum stripping of the solution at low pressure afforded phosphoric acid derivative (mixture of 70% ester and 30% acid) of tetramethylcyclotetrasiloxane.

A three necked 500 mL round bottom flask was charged with 1.6 g (0.00125 M) of the above product, 74 g (0.25M) octamethylcyclotetrasiloxane, 0.4 g (0.0025M) 1,3-divinyl-1,1,3,3-tetramethyldisiloxane and 1.0 g sulphuric acid. The solution was heated to 60 degrees Celsius and stirred at 60-65 degrees Celsius for 16 h. cool to 50 degrees Celsius and added 200 mL hexane, and 10 g moistened sodium bicarbonate. The resulting slurry was stirred for 6 h at 50-55 degrees Celsius. The solution was filtered, washed with hexane and the filtrate was vacuum stripped at low pressure to afford phosphate functional polydimethylsiloxane with terminal vinyl group. The polymer had a viscosity of 27.1 Pas at a shear rate of 10 rad/s when measured by a HAAKE Rheometer at 20 degrees Celsius.

Example 23

Phosphate Functional Polyorganosiloxane Bearing Terminal Hydride Groups

A three necked 500 mL round bottom flask was charged with 24.0 g (0.1 M) 1,3,5,7-tetramethylcyclotetrasiloxane, 68.0 g (0.41 M) eugenol and 0.001 g Platinum catalyst. Heat the solution to 60 degrees Celsius and stir the solution for 6 h. The solution was further stirred at 90-100 degrees Celsius for another 6 h to give eugenol functionalized cyclotetrasiloxane derivative.

A three necked 500 mL round bottom flask was charged with 17.9 g (0.02M) of the above product and 4.5 g (0.08 M) potassium hydroxide dissolved in 100 ml water. The solution was heated to 90-95 degrees Celsius and stirred at this temperature for about 2 h till dissolution. The solution was concentrated under vacuum till complete removal of water. 150 ml toluene was added and distilled 50 ml toluene to remove traces of water. The solution was maintained at 80 degrees Celsius while 15.5 g (0.08 M) Diethylchlorophosphate was added drop wise in 15 minutes. The solution was stirred at 80-90 degrees Celsius for 6 h. Solids formed were separated from the reaction mixture by filtration. The filtrate was washed with 2% sodium bicarbonate solution then with water. The vacuum stripping of the solution at low pressure afforded phosphate ester derivative of tetramethylcyclotetrasiloxane.

A three necked 250 mL round bottom flask was charged with 14 g (0.01 M) above product and 50 ml 6M HCl solution. Heat the solution to 90 degrees Celsius and stir for 6 h. The solution was cooled to room temperature and water was removed from the sticky product. The product was washed with water, dissolved in ethyl acetate, dried with sodium sulphate. The vacuum stripping of the solution at low pressure afforded phosphoric acid derivative (mixture of 70% ester and 30% acid) of tetramethylcyclotetrasiloxane.

A three necked 500 mL round bottom flask was charged with 1.6 g (0.00125M) of the above product, 74 g (0.25M) octamethylcyclotetrasiloxane, 0.33 g (0.0025M) 1,1,3,3-tetramethyldisiloxane and 1.0 g sulphuric acid. The solution was heated to 60 degrees Celsius and stirred at 60-65 degrees Celsius for 16 h. cool to 50 degrees Celsius and added 200 mL hexane, and 10 g moistened sodium bicarbonate. The resulting slurry was stirred for 6 h at 50-55 degrees Celsius. The solution was filtered, washed with hexane and the filtrate was vacuum stripped at low pressure to afford phosphate functional polydimethylsiloxane with terminal hydride group. The polymer had a viscosity of 37.6 Pas at a shear rate of 10 rad/s when measured by a HAAKE Rheometer at 20 degrees Celsius.

Example 24

Phosphate Functional Polyorganosiloxane Bearing Terminal Triethoxysilyl Groups

A three necked 500 mL round bottom flask was charged with 6 g (0.2 mM) of the product (from example 23), 0.075 g (0.4 mM) vinyltriethoxysilane and 0.001 g chloroplatinic acid. The solution was heated to 80 degrees Celsius and stirred at 80-90 degrees Celsius for 16 h to afford phosphate functional polydimethylsiloxane with terminal triethoxysilyl group.

Example 25

Phosphate Functional Polyorganosiloxane Bearing Terminal Polyether Groups

A three necked 500 mL round bottom flask was charged with 6 g (0.2 mM) of the product (from example 23), 0.18 g (0.4 mM) allyl terminated polyether (AM450 PEG from Clariant) and 0.001 g chloroplatinic acid. The solution was heated to 80 degrees Celsius and stirred at 80-90 degrees Celsius for 16 h to afford phosphate functional polydimethylsiloxane with terminal polyether group. The polymer had a viscosity of 21.7 Pas at a shear rate of 10 rad/s when measured by a HAAKE Rheometer at 20 degrees Celsius.

Example 26

Sulfonic Acid Functional Polyorganosiloxane Bearing Terminal Vinyl Groups

To the sulfonic acid functional cyclotetrasiloxane 8.26 g (8.0 mmol) obtained in Example 2, 474.5 g (1600.0 mmol) octamethyltetracyclosiloxane and 1.48 g (8.0 mmol) 1,1,3,3-tetramethyl-1,3-divinyldisiloxane were added and continued to stir at room temperature. After 6 h, an equilibrium of ~87 wt % of the linear siloxanes was reached to give sulfonic acid functional polydimethylsiloxane bearing terminal vinyl groups. The polymer had a viscosity of 29.7 Pas at a shear rate of 10 rad/s when measured by a HAAKE Rheometer at 20 degrees Celsius.

Example 27

Silver Salt of Sulfonic Acid Functional Polyorganosiloxane Bearing Terminal Vinyl Groups To the sulfonic acid functional polydimethylsiloxane 10.00 g (0.3 mmol) obtained in Example 24, 0.28 g (1.2 mmol) moistened silver oxide was added and continued to stir at 70 degrees Celsius for 6 h when the silver salt of sulfonic acid functional polydimethylsiloxane bearing terminal vinyl groups was obtained as viscous gum. The polymer had a viscosity of 55.8 Pas at a shear rate of 10 rad/s when measured by a HAAKE Rheometer at 20 degrees Celsius.

Example 28

Magnesium Salt of Sulfonic Acid Functional Polyorganosiloxane Bearing Terminal Vinyl Groups To the sulfonic acid functional polydimethylsiloxane 10.00 g (0.3 mmol) obtained in Example 24, 0.03 g (0.6 mmol) moistened magnesium oxide was added and continued to stir at 70 degrees Celsius for 6 h when the magnesium salt of sulfonic acid functional polydimethylsiloxane bearing terminal vinyl groups was obtained as viscous gum. The polymer had a viscosity of 508.6 Pas at a shear rate of 10 rad/s when measured by a HAAKE Rheometer at 20 degrees Celsius.

Example 29

Lithium Salt of Sulfonic Acid Functional Polyorganosiloxane Bearing Terminal Vinyl Groups To the sulfonic acid functional polydimethylsiloxane 10.00 g (0.3 mmol) obtained in Example 24, 0.03 g (1.2 mmol) moistened lithium hydroxide was added and continued to stir at 70 degrees Celsius for 6 h when the lithium salt of sulfonic acid functional polydimethylsiloxane bearing terminal vinyl groups was obtained as viscous gum. The polymer had a viscosity of 10.6 Pas at a shear rate of 10 rad/s when measured by a HAAKE Rheometer at 20 degrees Celsius.

Example 30

Triethylammoium salt of Sulfonic Acid Functional Polyorganosiloxane Bearing Terminal Vinyl Groups To the sulfonic acid functional polydimethylsiloxane 10.00 g (0.3 mmol) obtained in Example 0.12 g (1.2 mmol) triethyl amine was added and continued to stir at room temperature for 6 h when the triethylammonium salt of sulfonic acid functional polydimethylsiloxane bearing terminal vinyl groups was obtained as viscous gum. The polymer had a viscosity of 5.6 Pas at a shear rate of 10 rad/s when measured by a HAAKE Rheometer at 20 degrees Celsius.

What is claimed is:

1. A functionalized ionic silicone having formula (I):

$$M^1_a M^2_b M^3_c D^1_d D^2_e D^3_f T^1_g T^2_h T^3_i Q_j \quad (I)$$

wherein:
$M^1 = R^1 R^2 R SiO_{1/2}$
$M^2 = R^4 R^5 R^6 SiO_{1/2}$
$M^3 = R^7 R^8 R^9 SiO_{1/2}$
$D^1 = R^{10} R^{11} SiO_{2/2}$
$D^2 = R^{12} R^{13} SiO_{2/2}$
$D^3 = R^{14} R^{15} SiO_{2/2}$
$T^1 = R^{16} SiO_{3/2}$
$T^2 = R^{17} SiO_{3/2}$
$T^3 = R^{18} SiO_{3/2}$
$Q = SiO_{4/2}$ where $R^1, R^2, R^3, R^5, R^6, R^8, R^9, R^{10}, R^{11}, R^{13}, R^{15}, R^{16}$ are aliphatic, aromatic or fluoro containing monovalent hydrocarbon radicals containing from 1 to about 60 carbon atoms;

where $R^4, R^{12}, R^{17}$ are monovalent radical bearing ion-pairs having the formula (II):

$$-A-I^{x-}M_n^{y+}; \quad (II)$$

where A is a spacing group selected from a divalent hydrocarbon or hydrocarbonoxy group, where I is an ionic group selected from sulfonate —$SO_3^-$, sulfate —$OSO_3^{2-}$, carboxylate —$COO^-$, phosphonate —$PO_3^{2-}$ and phosphate —$OPO_3^{2-}$ group, where M is a cation independently selected from alkali metals, alkali earth metals, transition metals, metals, metal complexes, quaternary ammonium and phosphonium groups, organic cations, alkyl cations, cationic hydrocarbons and cationic biopolymers;

where $R^7, R^{18}$ are each independently monovalent organic radicals selected from —$OR^{20}$, hydrogen, unsaturated monovalent radicals, monovalent epoxy group-containing radicals, monovalent sulfur atom-containing radicals, monovalent organosilane groups and monovalent hydroxyl group containing radicals, and a monovalent hydrocarbon containing one or more of a halogen moiety, a carboxylate ester moiety, an imine moiety, an isocyanate moiety, an amide moiety, a nitrile moiety, or a tertiary amine containing other than alkyl groups moiety, where $R^{14}$ is each independently monovalent organic radicals selected from —$OR^{20}$, unsaturated monovalent radicals, monovalent epoxy group-containing radicals, monovalent sulfur atom-containing radicals, monovalent organosilane groups and monovalent hydroxyl group containing radicals, and a monovalent hydrocarbon containing one or more of a halogen moiety, a carboxylate ester moiety, an imine moiety, an isocyanate moiety, an amide moiety, a nitrile moiety, or a tertiary amine containing other than alkyl groups moiety, where $R^{20}$ is a monovalent hydrocarbon radical containing from 1 to about 60 carbon atoms or a heteroatom, where superscripts x and y are independently from 1 to 6 and x is a product of n and y where the subscript a, b, c, d, e, f, g, h, i, j are zero or positive subject to the following limitations: the sum a+b+c+d+e+f+g+h+i+j is greater than or equal to 2 and less than or equal to 6000, d+e+f is at least 1, b+e+h is greater than zero, c+f+i is greater than zero and a+b+c is greater than zero.

2. The functionalized ionic silicone of claim 1 wherein the monovalent hydrocarbon radical is independently selected from the group consisting of methyl, ethyl, n-propyl, isopropyl, n-butyl, isobutyl, tert-butyl, n-pentyl, iso-pentyl, neopentyl, tert-pentyl, hexyl, heptyl, octyl, isooctyl, 2,2,4-trimethylpentyl, nonyl, decyl, cycloalkyl radicals and aryl groups.

3. The functionalized ionic silicone of claim 2, wherein the cycloalkyl radicals are independently selected from the group consisting of cyclopentyl, cyclohexyl, cycloheptyl and methylcyclohexyl radicals.

4. The functionalized ionic silicone of claim 2 wherein the aryl radicals are independently selected from the group consisting of phenyl, naphthyl, o-, m- and p-tolyl, xylyl, ethylphenyl, and benzyl.

5. The functionalized ionic silicone of claim 1 wherein the divalent hydrocarbon group is an arylene group selected from the group consisting of —$(CHR')_k C_6 H_4 (CH_2)_l$—, —$CH_2 CH(R^1 R')(CH_2)_k C_6 H_4$—, and —$CH_2 CH(R')(CH_2)_k C_6 H_3 R''$—where R' is a hydrogen or defined by $R^1$, R" is a monovalent radical specifically from 1 to about 20 carbon atoms, sulfur atom(s), nitrogen atom(s), oxygen atom(s) or a radical containing combinations of the above atoms—where l has a value of 0 to 20, and k has a value of 0 to 20.

6. The functionalized ionic silicone of claim 1 wherein the divalent hydrocarbon group is an alkylene group of the formula —$(CHR^{19})_m$— where m has a value of 1 to about 20 and $R^{19}$ is hydrogen or $R^1$.

7. The functionalized ionic silicone of claim 1 including a divalent hydrocarbonoxy group selected from the group consisting of —$(CHR^{19})_m$—(O—$(CH(R^{19})CH_2$—O$)_{m'}$—$(CH_2)_l$ where $R^{19}$ is hydrogen or $R^1$, l has a value of from 1 to 20, and m has a value from 0 to 20 and m' has a value from 0 to 50.

8. The functionalized ionic silicone of claim 1 wherein $R^4$, $R^{12}$, and $R^{17}$ each have formula (II) and wherein in formula (II) M is a cation independently selected from Li, Na, K, Cs, Mg, Ca, Ba, Zn, Cu, Fe, Ni, Ga, Al, Mn, Cr, Ag, Au, Pt, Pd, Pb, Sb, Sn, Ru, Rh and their multivalent forms.

9. The functionalized ionic silicone of claim 1 wherein each of $R^7$, $R^{14}$ and $R^{18}$ are a monovalent radical selected from the group of the formulae (I) to (XI)

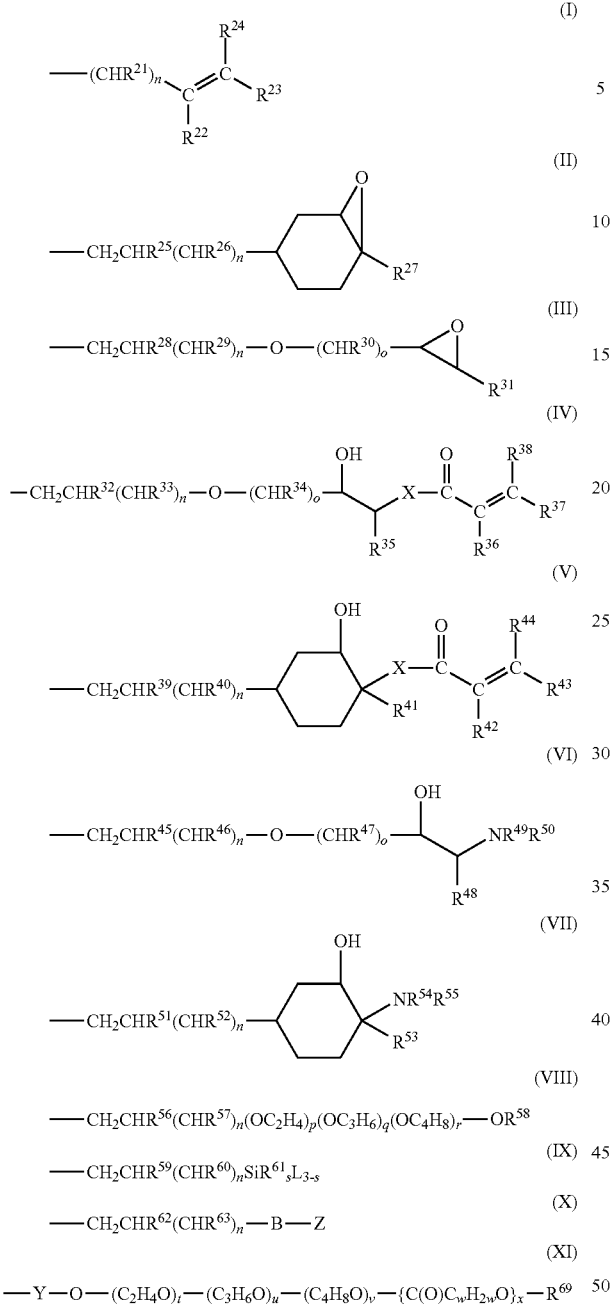

where R$^{21}$, R$^{26}$, R$^{29}$, R$^{30}$, R$^{33}$, R$^{34}$, R$^{40}$, R$^{46}$, R$^{47}$, R$^{52}$, R$^{63}$ are independently selected from —H, —OH, —R$^{66}$ and aliphatic/aromatic monovalent hydrocarbon having from 1 to about 60 carbon atoms, where R$^{22}$, R$^{23}$, R$^{24}$, R$^{25}$, R$^{27}$, R$^{28}$, R$^{31}$, R$^{32}$, R$^{35}$, R$^{36}$, R$^{37}$, R$^{38}$, R$^{39}$, R$^{41}$, R$^{42}$, R$^{43}$, R$^{44}$, R$^{45}$, R$^{48}$, R$^{51}$, R$^{53}$, R$^{56}$, R$^{57}$, R$^{59}$, R$^{60}$, R$^{61}$, R$^{62}$, are independently selected from hydrogen, aliphatic/aromatic monovalent hydrocarbon having from 1 to about 60 carbon atoms, where R$^{58}$ is aliphatic/aromatic monovalent hydrocarbon having from 2 to about 60 carbon atoms, where R$^{49}$, R$^{50}$, R$^{54}$, R$^{55}$ are independently selected from —H, —C$_t$H$_{2t}$OH and aliphatic/aromatic monovalent hydrocarbon having from 1 to about 60 carbon atoms, wherein t is a positive integer where L is a monovalent radical independently selected from halogen, OR$^{64}$, —CO(O)R$^{65}$, —N=CR$^{66}{}_2$, —NCO, —NC(O)R$^{67}$, —C≡N, —N=N and —NR$^{68}{}_2$ where R$^{64}$, R$^{65}$, R$^{66}$, R$^{67}$, R$^{68}$ are independently selected from a group consisting of hydrogen and alkyl, alkenyl, cycloalkyl and aryl containing from 1 to about 60 carbon atoms, where Z is a monovalent radical independently selected from halogen, OR$^{64A}$, —CO(O)R$^{65}$, —N=CR$^{66}{}_2$, —NCO, —NC(O)R$^{67}$, —C≡N, —N=N and —NR$^{68A}{}_2$ where R$^{65}$, R$^{66}$, R$^{67}$ are independently selected from a group consisting of hydrogen and alkyl, alkenyl, cycloalkyl and aryl containing from 1 to about 60 carbon atoms, and R$^{64A}$ is selected from a group consisting of alkyl, alkenyl, cycloalkyl and aryl containing from 2 to about 60 carbon atoms, and where R$^{68A}$ is selected from a group consisting of alkenyl, cycloalkyl and aryl containing from 2 to about 60 carbon atoms, where X is divalent radical selected from —CHR$^{65}$—, —O—, —NR$^{65}$— and —S— linkages, where Y and B are divalent radical selected from a linear, branched, cyclic hydrocarbon radical or aralkyl radical containing from 1 to about 60 carbon atoms;

where R$^{69}$ is a hydrogen or monovalent alkyl radical with 1 to about 20 carbon atoms or a heteroatom, where the subscript n is zero or positive integer and has a value in the range of 0 to about 60, where subscript o is positive integer and has a value in the range of 1 to about 60, where subscripts p, q and r are zero or positive and independently selected from a value in the range of 0 to about 100, subject to the limitation of p+q+r being greater than or equal to 1 and s is zero or positive integers and has a value of 0 to 2 where t, u, v and x can be zero or positive integers subject to the limitation t+u+v+x is greater than or equal to 1 and w is a positive integer.

10. The functionalized ionic silicone of claim 9 wherein each of R$^7$, R$^{14}$ and R$^{18}$ is a monovalent radical of formula (XI) and wherein R$^{69}$ is a monovalent alkyl radical containing from 1 to about 10 carbon atoms or an acyl group.

11. The functionalized ionic silicone of claim 10 wherein R$^{69}$ is a monovalent alkyl radical containing from 1 to about 8 carbon atoms or an acyl group.

12. The functionalized ionic silicone composition of claim 10 wherein R$^{69}$ is an epoxy group or an amine containing radical.

13. The functionalized ionic silicone of claim 1 wherein the ionic group is a sulfonate group.

14. The functionalized ionic silicone of claim 1 wherein the ionic group is a carboxylate group.

15. The functionalized ionic silicone of claim 1 wherein the ionic group is a phosphate group.

16. The functionalized ionic silicone of claim 1 wherein the silicone of formula (I) is selected from the group consisting of sulfonate functional polyorganosiloxane bearing terminal epoxy ether groups, sulfonate functional polyorganosiloxane bearing pendant epoxy ether groups, sulfonate functional polyorganosiloxane bearing pendant alkoxysilane groups, sulfonate functional polyorganosiloxane bearing terminal alkoxysilane groups, sulfonate functional polyorganosiloxane bearing terminal vinyl groups, sulfonate functional polyorganosiloxane bearing terminal polyether groups, sulfonate functional polyorganosiloxane bearing terminal silicon-hydride groups and sulfonate functional polyorganosiloxane bearing terminal acrylate groups.

17. A functionalized ionic silicone having formula (I):

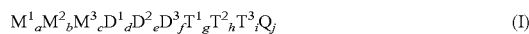

wherein:
$M^1 = R^1R^2RSiO_{1/2}$
$M^2 = R^4R^5R^6SiO_{1/2}$
$M^3 = R^7R^8R^9SiO_{1/2}$
$D^1 = R^{10}R^{11}SiO_{2/2}$
$D^2 = R^{12}R^{13}SiO_{2/2}$
$D^3 = R^{14}R^{15}SiO_{2/2}$
$T^1 = R^{16}SiO_{3/2}$
$T^2 = R^{17}SiO_{3/2}$
$T^3 = R^{18}SiO_{3/2}$
$Q = SiO_{4/2}$ where $R^1, R^2, R^3, R^5, R^6, R^8, R^9, R^{10}, R^{11}, R^{13}, R^{15}, R^{16}$ are aliphatic, aromatic or fluoro containing monovalent hydrocarbon radicals containing from 1 to about 60 carbon atoms;

where $R^4, R^{12}, R^{17}$ are monovalent radical bearing ion-pairs having the formula (II):

$$-A-I^{x-}M_n^{y+}; \qquad (II)$$

where A is a spacing group selected from a divalent hydrocarbon or hydrocarbonoxy group, where I is an ionic group selected from sulfonate —$SO_3^-$, sulfate —$OSO_3^{2-}$, carboxylate —$COO^-$, phosphonate —$PO_3^{2-}$ and phosphate —$OPO_3^{2-}$ group, where M is a cation independently selected from alkali metals, alkali earth metals, transition metals, metals, metal complexes, quaternary ammonium and phosphonium groups, organic cations, alkyl cations, cationic hydrocarbons and cationic biopolymers;

where $R^7, R^{18}$ are each independently monovalent organic radicals selected from —$OR^{20}$, hydrogen, unsaturated monovalent radicals, monovalent epoxy group-containing radicals, monovalent sulfur atom-containing radicals, monovalent organosilane groups and monovalent hydroxyl group containing radicals, and a monovalent hydrocarbon containing one or more of a halogen moiety, a carboxylate ester moiety, an imine moiety, an isocyanate moiety, an amide moiety, a nitrile moiety, or a tertiary amine containing other than alkyl groups moiety, where $R^{14}$ is each independently monovalent organic radicals selected from —$OR^{20}$, unsaturated monovalent radicals, monovalent epoxy group-containing radicals, monovalent sulfur atom-containing radicals, monovalent organosilane groups and monovalent hydroxyl group containing radicals, and a monovalent hydrocarbon containing one or more of a halogen moiety, a carboxylate ester moiety, an imine moiety, an isocyanate moiety, an amide moiety, a nitrile moiety, or a tertiary amine containing other than alkyl groups moiety, where $R^{20}$ is a monovalent hydrocarbon radical containing from 1 to about 60 carbon atoms or a heteroatom, where superscripts x and y are independently from 1 to 6 and x is a product of n and y where the subscript a, b, c, d, e, f, g, h, i, j are zero or positive subject to the following limitations: the sum a+b+c+d+e+f+g+h+i+j is greater than or equal to 2 and less than or equal to 6000, d+e+f is at least 1, b+e+h is greater than zero, c+f+i is greater than zero and a+b+c is greater than zero, wherein the silicone of formula (I) is a sulfonate functional polyorganosiloxane bearing a combination of two or more functional groups selected from the group consisting of terminal epoxy ether groups, pendant epoxy ether groups, pendant alkoxysilane groups, terminal alkoxysilane groups, terminal vinyl groups, pendant vinyl groups, terminal polyether groups, pendant polyether groups, terminal silicon-hydride groups, pendant silicon-hydride groups, terminal acrylate groups and pendant acrylate groups.

18. A composition containing the functionalized ionic silicone of claim 1 wherein the composition is in the form of an elastomer, a copolymer, a gel or an emulsion.

19. A catalyst containing the functionalized ionic silicone of claim 1 wherein the catalyst is a catalyst for acid-catalyzed ring opening polymerizations, a condensation reaction catalyst, or an addition reaction catalyst.

20. A macroinitiator for atom transfer radical polymerization or reversible addition fragmentation chain transfer polymerization reactions and comprising the functionalized ionic silicone of claim 1.

21. A healthcare composition comprising the functionalized ionic silicone of claim 1 and at least one healthcare agent.

22. The healthcare composition of claim 21 wherein the healthcare agent is selected from the group consisting of metals, metal ions, bioactives, anti-acne agents, anti-ageing agents, anti-caries agents, anti-fungal agents, anti-microbial agents, anti-oxidants, anti-cancer, anti-viral, anti-inflammatory, anti-coagulants, hemostatic agents, exfoliants, hormones, hormone analogs, enzymes, protein and peptides, medicinal compounds, biocides, external analgesics, oral care agents, oral care drugs, oxidizing agents, reducing agents, skin protectants, essential oils, insect repellents, UV light absorbing agents, solar filters, pigments, hydrating agents, vitamins and combinations thereof.

23. A healthcare product including the functionalized ionic silicone of claim 1, which further comprises one or more drug delivery systems, transdermal patches, wound healing patches, wound dressing patches, patches for scar reduction, transdermal iontophoresis, scaffold for tissue engineering, anti-microbial devices, wound management devices, ophthalmic devices, bioinserts, prostheses and body implants.

24. A personal care product including the functionalized ionic silicone of claim 1, and which further comprises one or more surfactants, emulsifiers, solvents, emollients, moisturizers, humectants, pigments, colorants, fragrances, biocides, preservatives, chelating agents, antioxidants, anti-microbial agents, anti-fungal agents, antiperspirant agents, exfoliants, hormones, hormone analogs, enzymes, protein and peptides, medicinal compounds, vitamins, alpha-hydroxy acids, beta-hydroxy acids, retinols, niacinamide, skin lightening agents, salts, electrolytes, alcohols, polyols, absorbing agents for ultraviolet radiation, botanical extracts, organic oils, waxes, thickening agents, particulate fillers, silicones, clays, plasticizers, occlusives, sensory enhancers, esters, resins, film formers, film forming agents or high refractive index materials.

25. A personal care product including the functionalized ionic silicone of claim 1, which takes the form of one or more of antiperspirant/deodorants, including sprays, sticks and roll-on products, shaving products, skin lotions, moisturizers, toners, bath products, cleansing products, shampoos, conditioners, combined shampoo/conditioners, mousses, styling gels, hair sprays, hair dyes, hair color products, hair bleaches, waving products, hair straighteners, nail polish, nail polish remover, nail creams and lotions, cuticle softeners, sunscreen, insect repellent, anti-aging products, lipsticks, foundations, face powders, eye liners, eye shadows, blushes, makeup, mascaras, moisturizing preparations, foundations, body and hand preparations, skin care preparations, face and neck preparations, tonics, dressings, hair grooming aids, aerosol fixatives, fragrance preparations, aftershaves, make-up preparations, soft focus applications, night and day skin care preparations, non-coloring hair preparations, tanning preparations, synthetic and non-synthetic soap bars, hand liquids, nose strips, non-woven applications for personal care, baby lotions, baby baths and shampoos, baby conditioners, shaving preparations, cucumber slices, skin pads, make-up removers, facial cleansing products, cold creams, sunscreen products, mousses, spritzes, paste masks and muds, face masks, colognes and toilet waters, hair cuticle coats, shower gels, face and body washes, personal care rinse-off products, gels, foam baths, scrubbing cleansers, astringents, nail conditioners, eye shadow sticks, powders for face or eye, lip balms, lip glosses, hair care pump sprays and other non-aerosol sprays, hair-frizz-control gels, hair leave-in conditioners, hair pomades, hair de-tangling products, hair fixatives, hair bleach products, skin lotions, pre-shaves and pre-electric shaves, anhydrous creams and lotions, oil/water, water/oil, multiple and macro and micro emulsions, water-resistant creams and lotions, anti-acne preparations, mouth-washes, massage oils, toothpastes, clear gels and sticks, ointment bases, topical wound-healing products, aerosol tales, barrier sprays, vitamin and anti-aging preparations, herbal-extract preparations, bath salts, bath and body milks, hair styling aids, hair-, eye-, nail- and skin-soft solid applications, controlled-release personal care products, hair conditioning mists, skin care moisturizing mists, skin wipes, pore skin wipes, pore cleaners, blemish reducers, skin exfoliators, skin desquamation enhancers, skin towelettes and cloths, depilatory preparations, personal care lubricants, nail coloring preparations, sunscreens, cosmetics, hair care products, skin care products, toothpastes, drug delivery systems for topical application of medicinal compositions that are to be applied to the skin and combinations comprising at least one of the foregoing products.

26. An anti-fouling composition including the functionalized ionic silicone and at least one anti-fouling agent, wherein the functionalized ionic silicone has formula (I):

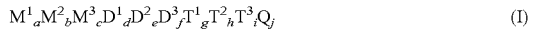 (I)

wherein:
$M^1 = R^1R^2RSiO_{1/2}$
$M^2 = R^4R^5R^6SiO_{1/2}$
$M^3 = R^7R^8R^9SiO_{1/2}$
$D^1 = R^{10}R^{11}SiO_{2/2}$
$D^2 = R^{12}R^{13}SiO_{2/2}$
$D^3 = R^{14}R^{15}SiO_{2/2}$
$T^1 = R^{16}SiO_{3/2}$
$T^2 = R^{17}SiO_{3/2}$
$T^3 = R^{18}SiO_{3/2}$
$Q = SiO_{4/2}$ where $R^1, R^2, R^3, R^5, R^6, R^8, R^9, R^{10}, R^{11}, R^{13}, R^{15}, R^{16}$ are aliphatic, aromatic or fluoro containing monovalent hydrocarbon radicals containing from 1 to about 60 carbon atoms;

where $R^4, R^{12}, R^{17}$ are monovalent radical bearing ion-pairs having the formula (II):

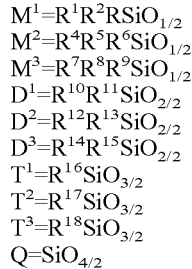

where A is a spacing group selected from a divalent hydrocarbon or hydrocarbonoxy group, where I is an ionic group selected from sulfonate $—SO_3^-$, sulfate $—OSO_3^{2-}$, carboxylate $—COO^-$, phosphonate $—PO_3^{2-}$ and phosphate $—OPO_3^{2-}$ group, where M is a cation independently selected from alkali metals, alkali earth metals, transition metals, metals, metal complexes, quaternary ammonium and phosphonium groups, organic cations, alkyl cations, cationic hydrocarbons and cationic biopolymers;

where $R^7, R^{18}$ are each independently monovalent organic radicals selected from $—OR^{20}$, hydrogen, unsaturated monovalent radicals, monovalent epoxy group-containing radicals, monovalent sulfur atom-containing radicals, monovalent organosilane groups and monovalent hydroxyl group containing radicals, and a monovalent hydrocarbon containing one or more of a halogen moiety, a carboxylate ester moiety, an imine moiety, an isocyanate moiety, an amide moiety, a nitrile moiety, or a tertiary amine containing other than alkyl groups moiety, where $R^{14}$ is each independently monovalent organic radicals selected from $—OR^{20}$, unsaturated monovalent radicals, monovalent epoxy group-containing radicals, monovalent sulfur atom-containing radicals, monovalent organosilane groups and monovalent hydroxyl group containing radicals, and a monovalent hydrocarbon containing one or more of a halogen moiety, a carboxylate ester moiety, an imine moiety, an isocyanate moiety, an amide moiety, a nitrile moiety, or a tertiary amine containing other than alkyl groups moiety, where $R^{20}$ is a monovalent hydrocarbon radical containing from 1 to about 60 carbon atoms or a heteroatom, where superscripts x and y are independently from 1 to 6 and x is a product of n and y where the subscript a, b, c, d, e, f, g, h, i, j are zero or positive subject to the following limitations: the sum a+b+c+d+e+f+g+h+i+j is greater than or equal to 2 and less than or equal to 6000, d+e+f is at least 1, b+e+h is greater than zero, c+f+i is greater than zero and a+b+c is greater than zero.

27. The anti-fouling product composition of claim 26 wherein the anti-fouling agent comprises one or more of cationic antifoulants, metal ions, metal-organic complexes, 4,5-dichloro-2-octyl-2H-isothiazole-3-on, benzalkonium chloride, or Zineb.

28. A paint, structural coating, masonry coating, or marine coating comprising the anti-fouling composition of claim 26.

29. An agricultural composition including the polyorganosiloxane of claim 1 and at least one agricultural agent.

30. The agricultural composition of claim 29, wherein the agricultural agent is selected from the group consisting of one or more of fertilizers, micronutrients, insecticides, herbicides, rodenticides and miticides.

31. A seed coating, superspreader or controlled release fertilizer comprising the agricultural composition of claim 29.

32. An automotive product, household product, paint, coating, laundry detergent, textile treatment, oil or gas product, fuel cell, electronic product, agriculture product, membrane, adhesive, sealant, injection moldable and compression moldable rubber or plastic, or silicone based rubber, comprising the functionalized silicone composition of claim 1.

33. A functionalized ionic silicone having formula (I):

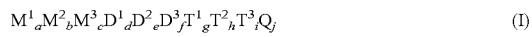 (I)

wherein:
$M^1 = R^1R^2RSiO_{1/2}$
$M^2 = R^4R^5R^6SiO_{1/2}$
$M^3 = R^7R^8R^9SiO_{1/2}$
$D^1 = R^{10}R^{11}SiO_{2/2}$
$D^2 = R^{12}R^{13}SiO_{2/2}$
$D^3 = R^{14}R^{15}SiO_{2/2}$
$T^1 = R^{16}SiO_{3/2}$
$T^2 = R^{17}SiO_{3/2}$
$T^3 = R^{18}SiO_{3/2}$
$Q = SiO_{4/2}$ where $R^1, R^2, R^3, R^5, R^6, R^8, R^9, R^{10}, R^{11}, R^{13}, R^{15}, R^{16}$ are aliphatic, aromatic or fluoro containing monovalent hydrocarbon radicals containing from 1 to about 60 carbon atoms;

where $R^4, R^{12}, R^{17}$ are monovalent radical bearing ion-pairs having the formula (II) or zwitterions having the formula (III):

$$-A-I^{x-}M_n^{y+};  \qquad (II)$$

where A is a spacing group selected from a divalent hydrocarbon or hydrocarbonoxy group, where I is an ionic group selected from sulfonate $-SO_3^-$, sulfate $-OSO_3^{2-}$, carboxylate $-COO^-$, phosphonate $-PO_3^{2-}$ and phosphate $-OPO_3^{2-}$ group, where M is a cation independently selected from alkali metals, alkali earth metals, transition metals, metals, metal complexes, quaternary ammonium and phosphonium groups, organic cations, alkyl cations, cationic hydrocarbons and cationic biopolymers;

$$—R'—NR''_2{}^+—R'''—I \qquad (III)$$

where R' is a divalent hydrocarbon radical containing from 1 to about 20 carbon atoms, where R'' is monovalent hydrocarbon radical containing from 1 to about 20 carbon atoms and where R''' is divalent hydrocarbon radical containing from 2 to about 20 carbon atoms;

where I is as defined above and, where $R^7, R^{18}$ are each independently monovalent organic radicals selected from hydrogen, monovalent epoxy group-containing radicals, monovalent sulfur atom-containing radicals, monovalent organosilane groups and monovalent hydroxyl group containing radicals, and a monovalent hydrocarbon containing one or more of an imine moiety, an isocyanate moiety, an amide moiety, a nitrile moiety, or a tertiary amine containing other than alkyl groups moiety, where $R^{14}$ is each independently monovalent organic radicals selected from monovalent epoxy group-containing radicals, monovalent sulfur atom-containing radicals, monovalent organosilane groups and monovalent hydroxyl group containing radicals, and a monovalent hydrocarbon containing one or more of an imine moiety, an isocyanate moiety, an amide moiety, a nitrile moiety, or a tertiary amine containing other than alkyl groups moiety, where superscripts x and y are independently from 1 to 6 and x is a product of n and y where the subscript a, b, c, d, e, f, g, h, i, j are zero or positive subject to the following limitations: the sum a+b+c+d+e+f+g+h+i+j is greater than or equal to 2 and less than or equal to 6000, d+e+f is at least 1, b+e+h is greater than zero, c+f+i is greater than zero and a+b+c is greater than zero.

\* \* \* \* \*